United States Patent
Pinchuk et al.

(10) Patent No.: US 9,616,140 B2
(45) Date of Patent: *Apr. 11, 2017

(54) FLUORESCENT PHOSPHOLIPID ETHER COMPOUNDS, COMPOSITIONS, AND METHODS OF USE

(71) Applicant: Cellectar, Inc., Madison, WI (US)

(72) Inventors: Anatoly Pinchuk, Madison, WI (US); Jamey P. Weichert, Fitchburg, WI (US); Marc Longino, Verona, WI (US); Irawati Kandela, Madison, WI (US); William R. Clarke, Colgate, WI (US)

(73) Assignee: CELLECTAR BIOSCIENCES, INC., Madison, WI (US)

( * ) Notice: Subject to any disclaimer, the term of this patent is extended or adjusted under 35 U.S.C. 154(b) by 171 days.

This patent is subject to a terminal disclaimer.

(21) Appl. No.: 14/493,489

(22) Filed: Sep. 23, 2014

(65) Prior Publication Data

US 2015/0044142 A1    Feb. 12, 2015

Related U.S. Application Data

(63) Continuation of application No. 13/318,546, filed as application No. PCT/US2010/034361 on May 11, 2010, now Pat. No. 8,871,181, which is a continuation of application No. 12/463,998, filed on May 11, 2009, now abandoned, and a continuation of application No. 12/463,983, filed on May 11, 2009, now abandoned, and a continuation of application No. 12/463,978, filed on May 11, 2009, now abandoned, and a continuation of application No. 12/463,970, filed on May 11, 2009, now Pat. No. 7,811,548, and a continuation of application No. 12/463,990, filed on May 11, 2009, now abandoned.

(51) Int. Cl.
| | | |
|---|---|---|
| A61B 5/00 | (2006.01) | |
| A61B 8/00 | (2006.01) | |
| A61B 10/00 | (2006.01) | |
| A61K 49/00 | (2006.01) | |
| C07F 9/572 | (2006.01) | |
| C07F 9/6558 | (2006.01) | |
| C07F 9/6561 | (2006.01) | |

(52) U.S. Cl.
CPC ...... *A61K 49/0021* (2013.01); *A61K 49/0032* (2013.01); *A61K 49/0052* (2013.01); *C07F 9/5728* (2013.01); *C07F 9/6561* (2013.01); *C07F 9/65583* (2013.01); *A61K 49/0017* (2013.01)

(58) Field of Classification Search
None
See application file for complete search history.

(56) References Cited

U.S. PATENT DOCUMENTS

| | | | |
|---|---|---|---|
| 4,925,649 | A | 5/1990 | Counsell et al. |
| 4,965,391 | A | 10/1990 | Counsell et al. |
| 5,087,721 | A | 2/1992 | Counsell et al. |
| 5,347,030 | A | 9/1994 | Counsell et al. |
| 5,369,097 | A | 11/1994 | Salari et al. |
| 5,626,654 | A | 5/1997 | Breton et al. |
| 5,728,529 | A | 3/1998 | Metzker et al. |
| 5,795,561 | A | 8/1998 | Counsell et al. |
| 6,417,384 | B1 | 7/2002 | Counsell et al. |
| 6,939,985 | B1 | 9/2005 | Marcuccio et al. |
| RE39,006 | E | 3/2006 | Houwen et al. |
| 7,041,859 | B1 | 5/2006 | Kabalka |
| 7,811,548 | B1 | 10/2010 | Pinchuk et al. |
| 8,022,235 | B2 | 9/2011 | Pinchuk et al. |
| 2002/0065429 | A1 | 5/2002 | Counsell et al. |
| 2007/0020178 | A1 | 1/2007 | Weichert et al. |
| 2007/0098633 | A2 | 5/2007 | Weichert et al. |
| 2007/0297988 | A1 | 12/2007 | Wu |
| 2008/0075660 | A1 | 3/2008 | Weichert et al. |
| 2009/0018357 | A1 | 1/2009 | Pinchuk et al. |
| 2010/0284929 | A1 | 11/2010 | Pinchuk et al. |

(Continued)

FOREIGN PATENT DOCUMENTS

| | | |
|---|---|---|
| CA | 2276284 A1 | 6/1998 |
| WO | WO 98/24480 | 6/1998 |

(Continued)

OTHER PUBLICATIONS

Examination report dated Jul. 28, 2014 for Application No. EP 10775385.7.
Extended European Search Report issued Jan. 18, 2013 for EP 10775385.7.
Japanese Office Action mailed May 13, 2014 for Application No. 2012-510929.
International Preliminary Report on Patentability for PCT/US2010/034361 mailed Nov. 24, 2011.

(Continued)

*Primary Examiner* — Michael G Hartley
*Assistant Examiner* — Melissa Perreira
(74) *Attorney, Agent, or Firm* — Wood, Phillips, Katz, Clark & Mortimer

(57) ABSTRACT

The invention generally relates to novel fluorescent phospholipid compounds, compositions comprising these compounds, and diagnostic methods utilizing these compounds. A preferred compound of the present invention has the following structural formula:

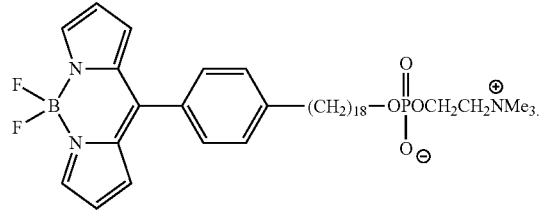

16 Claims, 12 Drawing Sheets

(56) References Cited

U.S. PATENT DOCUMENTS

| | | |
|---|---|---|
| 2010/0284930 A1 | 11/2010 | Pinchuk et al. |
| 2010/0284931 A1 | 11/2010 | Pinchuk et al. |
| 2010/0286510 A1 | 11/2010 | Pinchuk et al. |
| 2010/0316567 A1 | 12/2010 | Weichert et al. |
| 2012/0128596 A1 | 5/2012 | Pinchuk et al. |

FOREIGN PATENT DOCUMENTS

| | | |
|---|---|---|
| WO | WO 2004/009709 | 1/2004 |
| WO | WO 2005/063774 | 7/2005 |
| WO | WO 2005/084716 | 9/2005 |
| WO | WO 2008/150439 | 12/2008 |
| WO | WO 2009/121993 | 10/2009 |

OTHER PUBLICATIONS

International Search Report and Written Opinion for PCT/US2010/034361 mailed Aug. 30, 2010.

International Preliminary Report on Patentability for PCT/US2008/006842 mailed Dec. 10, 2009.

International Search Report and Written Opinion for PCT/US2008/006842 mailed Sep. 2, 2008.

Invitation to Pay Additional Fees for PCT/US2010/038294 mailed Jul. 23, 2010.

International Preliminary Report on Patentability for PCT/US2007/017885 mailed Feb. 26, 2009.

International Search Report for PCT/US2007/017885 mailed Aug. 14, 2008.

Written Opinion for PCT/US2007/017885 dated Jul. 31, 2008.

Office Communication for U.S. Appl. No. 12/463,983 mailed May 26, 2011.

Office Communication for U.S. Appl. No. 13/318,546 mailed Jan. 27, 2013.

Office Communication for U.S. Appl. No. 13/318,546 mailed Dec. 4, 2013.

Notice of Allowance mailed Jun. 23, 2014 for U.S. Appl. No. 13/318,546.

Office Communication for U.S. Appl. No. 12/463,970 mailed Mar. 2, 2010.

Notice of Allowance for U.S. Appl. No. 12/463,970 mailed Jul. 26, 2010.

Office Communication for U.S. Appl. No. 12/463,978 mailed Apr. 12, 2011.

Office Communication for U.S. Appl. No. 12/463,990 mailed Apr. 14, 2011.

Office Communication for U.S. Appl. No. 12/463,998 mailed Jun. 9, 2011.

Office Communication for U.S. Appl. No. 12/156,258 mailed Oct. 5, 2010.

Notice of Allowance for U.S. Appl. No. 12/156,258 mailed Apr. 14, 2011.

Office Communication for U.S. Appl. No. 11/891,939 mailed Dec. 3, 2008.

[No Authors Listed] IR-775 chloride—Substance Summary. PubChem Substance. Available at http://pubchem.ncbi.nlm.nih.gov/summary/summary.cgi?sid=24878794. Last accessed Jun. 23, 2010. 1 page.

[No Authors Listed] Modulation of fluorouracil by leucovorin in patients with advanced colorectal cancer: evidence in terms of response rate. Advanced Colorectal Cancer Meta-Analysis Project. J Clin Oncol. Jun. 1992;10(6):896-903.

[No Authors Listed] Synthesis and evulation of radioiodinated phospholipid ethers for imaging of prosate cancer. Quart J Nucl Med. 1997;41(Suplp 1 to No. 2):14-6.

Arthur et al., The inhibition of cell signaling pathways by antitumor ether lipids. Biochim Biophys Acta. Feb. 5, 1998;1390(1):85-102.

Becher et al., Phase II Trial of Orally Administered Miltefosine in Advanced Colorectal Cancer. Onkologie. 1993;16:11-5.

Berdel et al., Daily Oral Miltefosine (Hexadecy Phosphocholin) in Patients with Advanced Non-Small Cell Lung Cancer. A Phase II Study. Onkologie. 1992;15:238-42.

Clezy et al., The Chemistry of Pyrrolic Compounds. VIII. Dipyrrylthiones. Aust J Chem. 1969;22:239-49.

Counsell et al., Tumor visualization with a radioiodinated phospholipid ether. J Nucl Med. Mar. 1990;31(3):332-6.

Crul et al., Phase I and pharmacological study of daily oral administration of perifosine (D-21266) in patients with advanced solid tumours. Eur J Cancer. Aug. 2002;38(12):1615-21.

Curley et al., Radiofrequency ablation of unresectable primary and metastatic hepatic malignancies: results in 123 patients. Ann Surg. Jul. 1999;230(1):1-8.

De Gramont et al., Randomized trial comparing monthly low-dose leucovorin and fluorouracil bolus with bimonthly high-dose leucovorin and fluorouracil bolus plus continuous infusion for advanced colorectal cancer: a French intergroup study. J Clin Oncol. Feb. 1997;15(2):808-15.

Drummen et al., C11-BODIPY(581/591), an oxidation-sensitive fluorescent lipid peroxidation probe: (micro)spectroscopic characterization and validation of methodology. Free Radic Biol Med. Aug. 15, 2002;33(4):473-90.

Elvington et al. Fluorescent, acyl chain-labeled phosphatidylcholine analogs reveal novel transport pathways across the plasma membrane of yeast. J Biol Chem. Dec. 9, 2005;280(49):40957-64.

Fong et al., Clinical score for predicting recurrence after hepatic resection for metastatic colorectal cancer: analysis of 1001 consecutive cases. Ann Surg. Sep. 1999;230(3):309-18; discussion 318-21.

Giacchetti et al., Phase III multicenter randomized trial of oxaliplatin added to chronomodulated fluorouracil-leucovorin as first-line treatment of metastatic colorectal cancer. J Clin Oncol. Jan. 2000;18(1):136-47.

Goncalves, Fluorescent labeling of biomolecules with organic probes. Chem Rev. Jan. 2009;109(1):190-212.

Goud et al., Synthesis of 8-heteroatom-substituted 4,4-difluoro-4-bora-3a, 4a-diaza-s-indacene dyes (BODIPY). Tetrahedron. 2006;62:5084-91.

Greven et al., Can positron emission tomography distinguish tumor recurrence from irradiation sequelae in patients treated for larynx cancer? Cancer J Sci Am. Nov.-Dec. 1997;3(6):353-7.

Hornillos et al., Synthesis of BODIPY-labeled alkylphosphocholines with leishmanicidal activity, as fluorescent analogues of miltefosine. Bioorg Med Chem Lett. Dec. 15, 2008;18(24):6336-9. Epub Nov. 1, 2008.

Ike et al., Results of aggressive resection of lung metastases from colorectal carcinoma detected by intensive follow-up. Dis Colon Rectum. Apr. 2002;45(4):468-73; discussion 473-5.

Imboden et al., The level of MHC class I expression on murine adenocarcinoma can change the antitumor effector mechanism of immunocytokine therapy. Cancer Res. Feb. 15, 2001;61(4):1500-7.

Kabalka et al., Synthesis of radioiodinated aryl iodides via boronate precursors. Nucl Med Biol. Nov. 2002;29(8):841-3. Abstract only.

Kallman, Commentary on Part 5. In: Rodent tumor models in experimental cancer therapy. Pergamon Press. New York. 1987:111-32.

Kim et al., Synthesis and spectroscopic properties of a new 4-bora-3a,4a-diaza-s-indacene (BODIPY®) dye. Chem Commun. 1999:1889-90.

Lager et al., Novel meso-polyarylamine-BODIPY hybrids: synthesis and study of their optical properties. J Org Chem. Mar. 6, 2009;74(5):2053-8.

Lencioni et al., Percutaneous radiofrequency thermal ablation of liver malignancies: techniques, indications, imaging findings, and clinical results. Abdom Imaging. Jul.-Aug. 2001;26(4):345-60.

Li et al., Synthesis and spectral properties of cholesterol- and FTY720-containing boron dipyrromethene dyes. J Org Chem. Oct. 26, 2007;72(22):8376-82. Epub Oct. 3, 2007.

Liebeskind et al., Heteroaromatic thioether-boronic acid cross-coupling under neutral reaction conditions. Org Lett. Mar. 21, 2002;4(6):979-81.

(56) References Cited

OTHER PUBLICATIONS

Longino, M.A. et al., Tumor Selective Rentention of NM404—Involvement of Phospholipase D. Molecular Imag. 2004;3(3). Abstract 257. Abstract ID 290.
Loudet et al., BODIPY dyes and their derivatives: syntheses and spectroscopic properties. Chem Rev. Nov. 2007;107(11):4891-932. Epub Oct. 9, 2007.
Maier et al., Fluorescent lipid probes: some properties and applications (a review). Chem Phys Lipids. Jun. 2002;116(1-2):3-18.
Mayr et al., Method and timing of tumor volume measurement for outcome prediction in cervical cancer using magnetic resonance imaging. Int J Radiat Oncol Biol Phys. Jan. 1, 2002;52(1):14-22.
Mollinedo, Antitumour ether lipids: proapoptotic agents with multiple therapeutic indications. Expert Opin Ther Patents. 2007;17(4):385-405.
Moser et al., Specificity of NM404 for Hyperplasia versus Neoplasia in the ApcMin/+ Endogenous Mammary Adenocarcinoma Model. Online Aug. 15-18, 2003 Presentation No. 305.
Noh et al., Overexpression of phospholipase D1 in human breast cancer tissues. Cancer Lett. Dec. 20, 2000;161(2):207-14. Abstract only.
O'Dwyer et al., Follow-up of stage B and C colorectal cancer in the United States and France. Semin Oncol. Feb. 2001;28(1 Suppl 1):45-9.
Oshimoto et al., Increased activity and expression of phospholipase D2 in human colorectal cancer. Oncol Res. 2003;14(1):31-7.
Pena-Cabrera et al., Simple, general, and efficient synthesis of meso-substituted borondipyrromethenes from a single platform. Org Lett. Sep. 27, 2007;9(20):3985-8. Epub Sep. 1, 2007.
Penna et al., Colorectal metastasis (liver and lung). Surg Clin North Am. Oct. 2002;82(5):1075-90, x-xi.
Peters et al., Synthesis of borondipyrromethene (BODIPY)-labeled sphingosine derivatives by cross-metathesis reaction. J Org Chem. Mar. 2, 2007;72(5):1842-5. Epub Jan. 24, 2007.
Pickhardt et al., Computed tomographic virtual colonoscopy to screen for colorectal neoplasia in asymptomatic adults. N Engl J Med. Dec. 4, 2003;349(23):2191-200. Epub Dec. 1, 2003.
Pinchuk et al., Synthesis and structure-activity relationship effects on the tumor avidity of radioiodinated phospholipid ether analogues. J Med Chem. Apr. 6, 2006;49(7):2155-65.
Plotzke et al., Selective localization of radioiodinated alkylphosphocholine derivatives in tumors. Int J Rad Appl Instrum B. Oct. 1992;19(7):765-73.
Plotzke et. al., Selective localization of a radioiodinated phospholipid ether analog in human tumor xenografts. J Nucl Med. May 1993;34(5):787-92.
Quesada et al., Fluorescent phenylpolyene analogues of the ether phospholipid edelfosine for the selective labeling of cancer cells. J Med Chem. Oct. 21, 2004;47(22):5333-5.
Quon, et al., "Flying through" and "flying around" a PET/CT scan: Pilot study and development of 3D integrated 18F-FDG PET/CT for virtual bronchoscopy and colonoscopy. J Nucl Med. Jul. 2006;47(7):1081-7.
Rampy et al., Biological disposition and imaging of a radioiodinated alkylphosphocholine in two rodent models of breast cancer. J Nucl Med. Sep. 1996;37(9):1540-5.
Rampy et al., Synthesis and biological evaluation of radioiodinated phospholipid ether stereoisomers. J Med Chem. Aug. 4, 1995;38(16):3156-62.
Sakharov et al., Prolonged lipid oxidation after photodynamic treatment. Study with oxidation-sensitive probe C11-BODIPY581/591. FEBS Lett. Feb. 14, 2005;579(5):1255-60. Epub Jan. 26, 2005.
Saltz et al., Irinotecan plus fluorouracil and leucovorin for metastatic colorectal cancer. Irinotecan Study Group. N Engl J Med. Sep. 28, 2000;343(13):905-14.

Sandgren et al., Evaluation of 125I-NM404 in a Spontaneous Murine Pancreatic Adenocarcinoma Model. Aug. 2003, 2nd Annual Meeting of the Society of Molecular Imaging, San.
Saugar et al., Synthesis and biological evaluation of fluorescent leishmanicidal analogues of hexadecylphosphocholine (miltefosine) as probes of antiparasite mechanisms. J Med Chem. Nov. 29, 2007;50(24):5994-6003. Epub Oct. 31, 2007.
Sik Min et al., Neoplastic transformation and tumorigenesis associated with overexpression of phospholipase D isozymes in cultured murine fibroblasts. Carcinogenesis. Oct. 2001;22(10):1641-7.
Snyder et al., Alkyl and alk-1-enyl ethers of glycerol in lipids from normal and neoplastic human tissues. Cancer Res. Jan. 1969;29(1):251-7.
Snyder et al., Occurrence and nature of 0-alkyl and O-alk-I-enyl moieties of glycerol in lipids of Morris transplanted hepatomas and normal rat liver. Biochim Biophys Acta. Apr. 29, 1969;176(3):502-10.
Solbiati et al., Percutaneous radio-frequency ablation of hepatic metastases from colorectal cancer: long-term results in 117 patients. Radiology. Oct. 2001;221(1):159-66.
Stahl et al., PET/CT molecular imaging in abdominal oncology. Abdom Imaging. May-Jun. 2004;29(3):388-97.
Terwogt et al., Phase II trial of topically applied miltefosine solution in patients with skin-metastasized breast cancer. Br J Cancer. Mar. 1999;79(7-8):1158-61.
Ulrich et al., The chemistry of fluorescent bodipy dyes: versatility unsurpassed. Angew Chem Int Ed Engl. 2008;47(7):1184-201.
Umezawa et al., Bright, color-tunable fluorescent dyes in the Vis/NIR region: establishment of new "tailor-made" multicolor fluorophores based on borondipyrromethene. Chemistry. 2009;15(5):1096-106.
Umezawa et al., Bright, color-tunable fluorescent dyes in the visible-near-infrared region. J Am Chem Soc. Feb. 6, 2008;130(5):1550-1. Epub Jan. 15, 2008.
Wagner et al., Boron-dipyrromethene dyes for incorporation in synthetic multi-pigment light-harvesting arrays. Pure & Appl Chem. 1996;68(7):1373-80.
Wang et al., Molecular imaging with 123I-FIAU, 18F-FUdR, 18F-FET, and 18F-FDG for monitoring herpes simplex virus type 1 thymidine kinase and ganciclovir prodrug activation gene therapy of cancer. J Nucl Med. Jul. 2006;47(7):1161-71.
Weber et al., Interleukin-12 gene transfer results in CD8-dependent regression of murine CT26 liver tumors. Ann Surg Oncol. Mar. 1999;6(2):186-94.
Weichert et al., Initial Clinical Imagining Results with NM404 in Non-Small Cell Lung Cancer. Molec Imag. 2004;3(3):269-70.
Weichert et al., Polyiodinated triglyceride analogs as potential computed tomography imaging agents for the liver. J Med Chem. Feb. 17, 1995;38(4):636-46.
Weichert et al., Radioiodination via Isotope Exchange in Pivalic Acid. Appl Radiat Isot. 1986;37(8):907-13.
Weichert et al., Specificity of NM404 for Hyperplasia versus Neoplasia in the ApcMin/+ Endogenous Mammary Adenocarcinoma Model. 2nd Annual Meeting of the Society of Molecular Imaging. San Fransico. Aug. 15-18, 2003. Presentation No. 305. Abstract only. 1 page. Retrieved from the Internet on Jan. 27, 2006 at http://www.abstractsonline.com/viewer/viewAbstract.asp?CKey={175C0489-C808-47DF-B4EF-5CF57EE52265}&MKey={4C56C7C9-3CB4-404E-A0C1-3F37525A5245}&AKey={A4C6DD8F-4BF2-400D-97ED-20C14381CDBB}&SKey={0AAB7B18-F58E-4226-A5DF-755F3585A60F}.
Wichmann et al., Carcinoembryonic antigen for the detection of recurrent disease following curative resection of colorectal cancer. Anticancer Res. Nov.-Dec. 2000;20(6D):4953-5.
Zasadny et al., Predicted dosimetry for I-131-NM-404, a phospholipid ether agent for tumor imaging and possible therapy. J Nucl Med. 1999;40(5):39P.

A375 (skin melanoma)

704sk (normal skin)

A375 (skin melanoma)

A375 (skin melanoma)

HCT-116 (Colorectal adenocarcinoma)

MES SA/Dx5 (Uterine sarcoma)

Mia Paca-2 (Pancreatic carcinoma)

Panc-1 (Pancreatic carcinoma)

Ovcar-3 (ovarian adenocarcinoma)

Ovcar-3 (ovarian adenocarcinoma)

U-87MG (Glioblastoma)

NFA (normal fibroblast)

Caki-2 (clear cell carcinoma)

PC3 (prostate adenocarcinoma)

U-87MG (Glioblastoma)

NFA and PC3 Cell Lines

NFA and Caki-2 Cell Lines

Athymic Mice With Pancreatic Carcinoma

Tumors Excised From Athymic Mice With Pancreatic Carcinoma

CLR1401 Administered Prior to Imaging

| A | B | C | D |
|---|---|---|---|
| 24 hr (IV) | 96 hr (IV) | 24 hr (Oral) | 96 hr (Oral) |

HCT-116 tumor-bearing mouse

Panc-1 tumor-bearing mouse

Panc-1 tumor-bearing mouse

FLUORESCENT PHOSPHOLIPID ETHER COMPOUNDS, COMPOSITIONS, AND METHODS OF USE

RELATED APPLICATIONS

This application is a continuation of U.S. patent application Ser. No. 13/318,546, filed Nov. 2, 2011, which is a national stage filing under 35 U.S.C. §371 of International PCT Patent Application No. PCT/US2010/034361, filed May 11, 2010, entitled "Fluorescent Phospholipid Ether Compounds, Compositions, and Methods of Use," by Pinchuk et al., which is a continuation-in-part of each of U.S. patent application Ser. No. 12/463,983, filed May 11, 2009, entitled "Use of Fluorescent Phospholipid Ether Compounds in Biopsies," by Pinchuk et al.; U.S. patent application Ser. No. 12/463,978, filed May 11, 2009, entitled "Fluorescent Imaging of Tumors Using Phospholipid Ether Compounds," by Pinchuk et al.; U.S. patent application Ser. No. 12/463,970, filed May 11, 2009, entitled "Fluorescent Phospholipid Ether Compounds and Compositions," by Pinchuk et al.; U.S. patent application Ser. No. 12/463,990, filed May 11, 2009, entitled "Fluorescent Imaging of Skin Cancers Using Phospholipid Ether Compounds," by Pinchuk et al.; and U.S. patent application Ser. No. 12/463,998, filed May 11, 2009, entitled "Fluorescent Phospholipid Ether Compounds, Compositions, and Methods of Use," by Pinchuk et al. Each of these is incorporated herein by reference.

FIELD OF THE INVENTION

The invention generally relates to fluorescent tumor-selective phospholipid ether (PLE) compounds, compositions comprising these compounds, and methods of using these compounds and compositions in various diagnostic applications.

BACKGROUND

It is known that earlier tumor detection leads to the improvement of long-term survival. Therefore, the development of more selective and noninvasive tumor diagnostic techniques is a high priority. Fluorescent imaging has proven to be an efficient tool for preclinical cancer research, anti-tumor drug discovery and pharmacological developments by providing images of the bio-distribution of fluorescent markers. By tagging regions of interest with tumor-specific fluorescent molecular probes, this technique enables visualization of location and geometries of malignant areas.

The fundamental barriers to optical imaging in tissue are high light scattering, autofluorescence, and high absorption by hemoglobin in the mid-visible band. Use of red and near-infrared light is the most basic step towards improved imaging. Moving to near-infrared wavelengths (700-1100 nm) confers other advantages for imaging mammalian tissues: less background fluorescence is excited, since autofluorescence in tissues is mostly excited by near ultraviolet and blue light; and less autofluorescence interferes, since fluorescence from most mammalian tissues peaks in the yellow and is very low beyond 650 nm. (Ballou B, Ernst L A, Waggoner A S. *Curr. Med. Chem.*, 2005, 12, 795-805; Fabian J, Nakazumi H, Matsuoka M. *Chem. Rev.*, 1992, 92, 1197-1226). The use of near-IR fluorescence improves in many ways the performance of fluorescence-based biological assays. For example, the near-IR fluorescence provides: 1) significant reduction of background autofluorescence; 2) deeper light penetration; 3) minimal photodamage to biological tissue; 4) less sensitivity to the optical properties of the media. A good fluorescent label should have large extinction coefficient, high fluorescent quantum yield and high photostability.

Endoscopy, in particular, colonoscopy and bronchoscopy, is utilized to find abnormal growth and tumors protruding into the lumen. A device, called endoscope, is inserted into a body cavity. Traditionally, endoscopes use a daylight channel, i.e. the observer sees all finding at the wavelength of naturally occurring light.

Lately, newer endoscopes have the ability to utilize several channels, i.e. a daylight channel and one or more additional channels at other light wavelengths. These additional channels are used to monitor either naturally occurring fluorescence or fluorescence of a dye that was either injected into the body or sprayed onto the body cavity surface. One of the possible channels is in the NIR (near infrared) area. The advantage of the NIR area is that the light absorption in the NIR area (usually 600-800 nm) is minimal, and fluorescence can be detected at a depth of a few millimeters to nearly a centimeter beneath the surface of the body cavity. It is believed that this has advantages to detect tumors and lymph node metastases in organs such as colon and lung.

Accordingly, the need exists to further explore the uses of near infrared fluorescence in detecting malignancies during the endoscopic process.

SUMMARY OF THE INVENTION

The invention generally relates to phospholipid ether (PLE) compounds, compositions comprising these compounds, and the use of the compounds and/or compositions in diagnosis of various malignancies.

In one embodiment, the present invention relates to phospholipid fluorescent compounds according to formulas (I)-(VI):

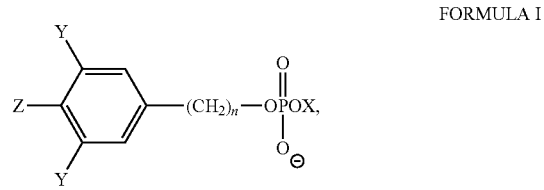

FORMULA I

FORMULA II wherein n is an integer between 7 and 23;
Y is H, Me or Et;
Z is a fluorophore; and
X is selected from the group consisting of

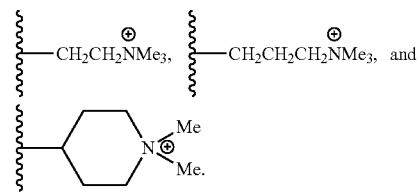

In a preferred embodiment, Z is selected from the following:

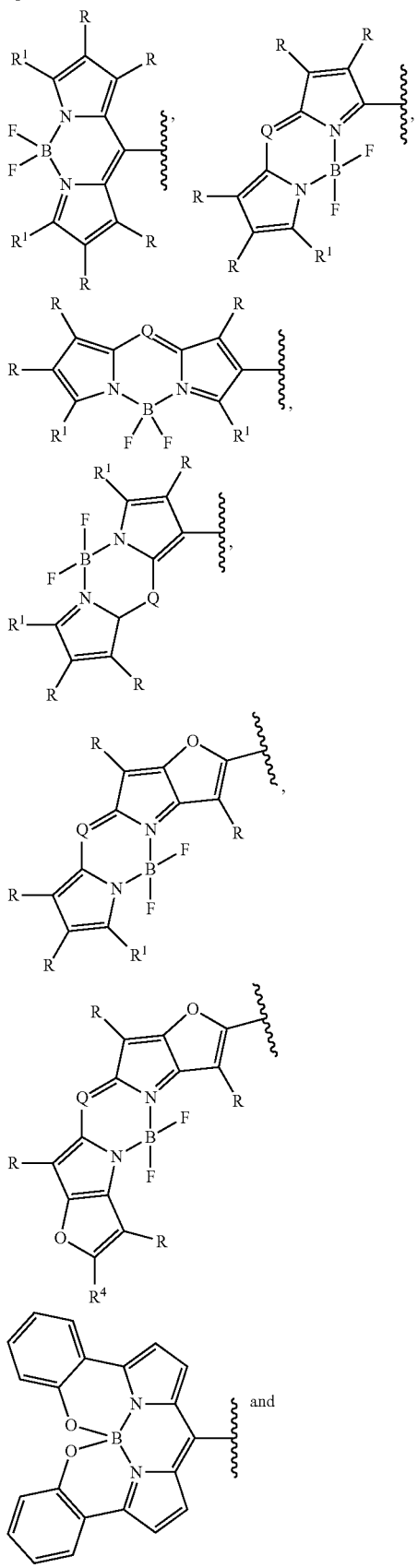

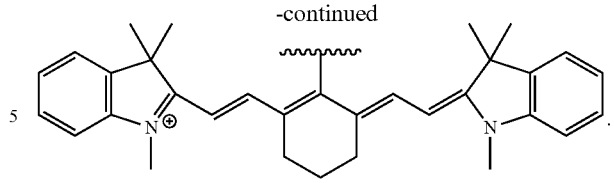

wherein R is selected from the group consisting of H, Me, Et, Br and I.

Q is selected from the group consisting of N, CH, C-Me, C-Et, C—CF$_3$, C-Ph

R$^1$ is selected from the group consisting of

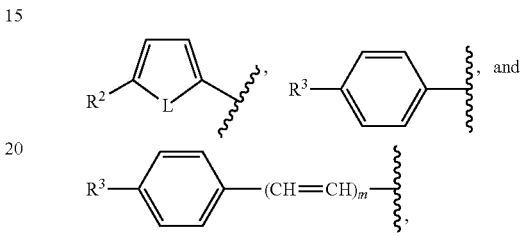

L is selected from the group consisting of O, S, NH and NMe;

R$^2$ is selected from the group consisting of H, Me, and Et;

R$^3$ is selected from the group consisting of H, OMe, OEt, and NMe$_2$;

R$^4$ is selected from the group consisting of H, Me, Et, Ph or p-methoxy-phenyl; and m is an integer from 1 to 5.

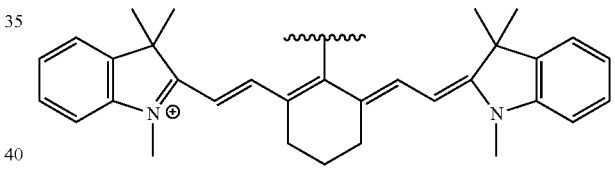

(or other positively charged fluorophores) may also include a negatively charged counterion, such as Cl$^-$.

FORMULA III

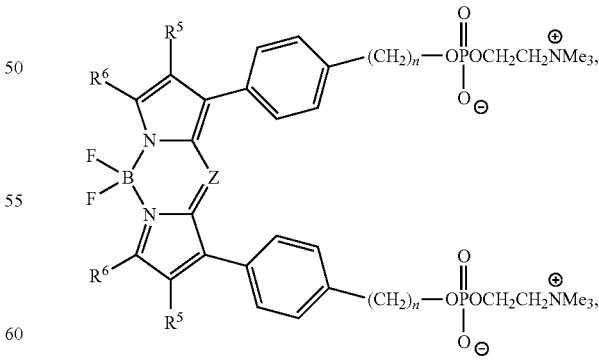

wherein R$^5$ is selected from the group consisting of H, Me, Et, Br and I;

R$^6$ is selected from the group consisting of H, Me, Et, p-methoxy-phenyl, p-(N,N-dimethylamino)-phenyl and

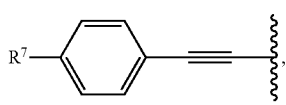

wherein $R^7$ is selected from the group consisting of H, Me, OMe, and $Me_2N$.

FORMULA IV

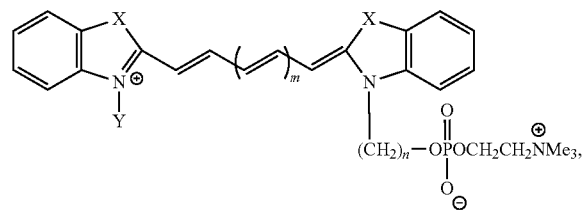

wherein n is an integer between 7 and 23;
m is an integer between 0 and 4;
X is selected from the group consisting of O, S, $CMe_2$, and $C=CH_2$;
Y is selected from the group consisting of Me, Et, Pr, i-Pr and

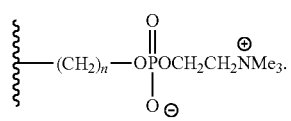

FORMULA V

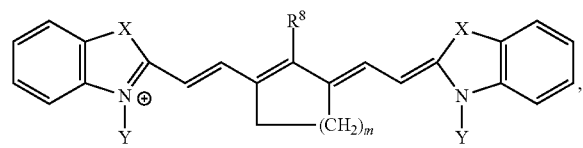

wherein m is an integer between 0 and 4;
X is selected from the group consisting of O, S, $CMe_2$ and $C=CH_2$;
Y is selected from the group consisting of Me, Et, Pr and i-Pr;
$R^8$ is selected from the group consisting of

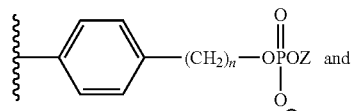

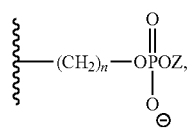

wherein n is an integer between 7 and 23; and
Z is selected from the group consisting of

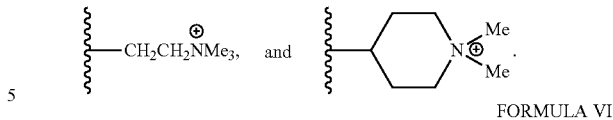

FORMULA VI

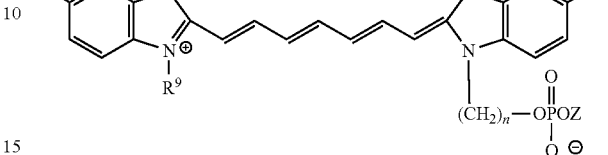

wherein n is an integer between 7 and 23
$R^9$ is selected from the group consisting of Me, Et and

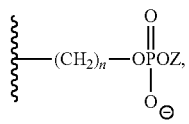

Z is selected from the group consisting of

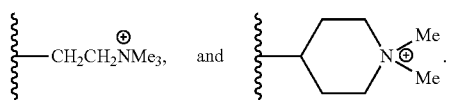

In a preferred embodiment, the invention relates to a compound having a formula:

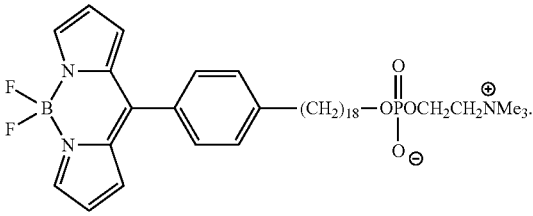

The invention also generally relates to compositions comprising the compounds of the present invention.

The invention also generally relates to various methods of using the compounds of the present invention, including, but not limited to, endoscopic determination of the presence of internal malignancy; visual and/or microscopically added determination of the presence of malignant lesions on the skin; aiding in the selection of biopsy tissues in internal and skin malignancies; determination of the presence of internal and/or skin malignancies during surgeries to aid the complete biopsy and/or surgical resection of said malignancies.

DETAILED DESCRIPTION OF THE INVENTION

Figure 1A:
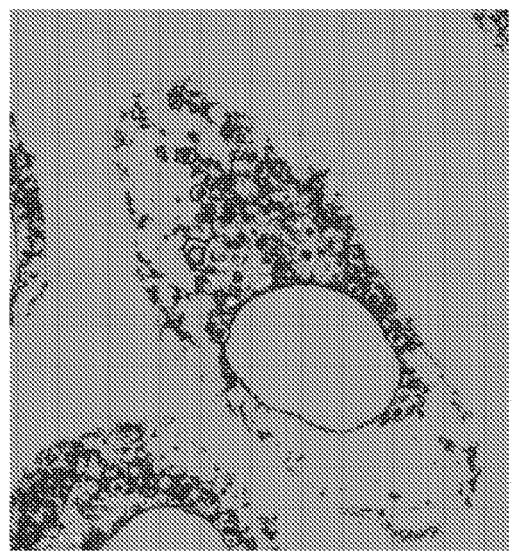
FIG. 1a depicts skin melanoma (A375) cells after 24 hour incubation with CLR1501.

As used herein, the term "alkyl" includes straight chained and branched hydrocarbon groups containing the indicated number of carbon atoms, typically methyl, ethyl, and straight chain and branched propyl and butyl groups. The term "alkyl" also encompasses cycloalkyl, i.e., a cyclic $C_3$-$C_8$ hydrocarbon group, such as cyclopropyl, cyclobutyl, cyclopentyl, and cyclohexyl. Reference to an individual group or moiety, such as "propyl," embraces only the straight chain group or moiety. A branched chain isomer, such as "isopropyl," is specifically referred to.

"Me" refers to methyl.

"Et" refers to ethyl.

"Ph" refers to phenyl.

"Pr" refers to propyl.

"i-Pr" refers to iso-propyl.

The singular articles "a", "an," and "the" include plural reference unless specifically indicated or unless it is clear from the context that only the singular form is possible.

The terms "phospholipid ether compound" and "phospholipid compound" are used interchangeably for the purposes of the present application.

In one embodiment, the present invention generally relates to fluorescent PLE compounds and various methods of their use for malignancy determination and other uses.

In one embodiment, the invention generally refers to phospholipid fluorescent dyes according to formulas (I)-(VI):

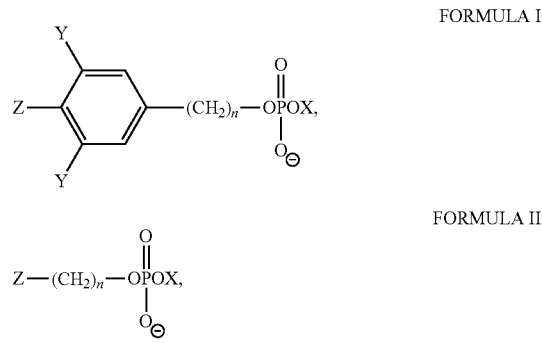

wherein n is an integer between 7 and 23;

Y is H, Me or Et;

Z is a fluorophore; and

X is selected from the group consisting of

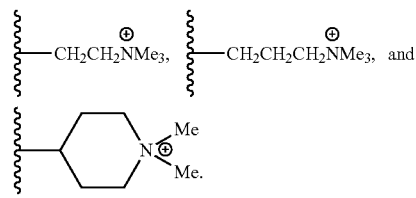

In a preferred embodiment, Z is selected from the following:

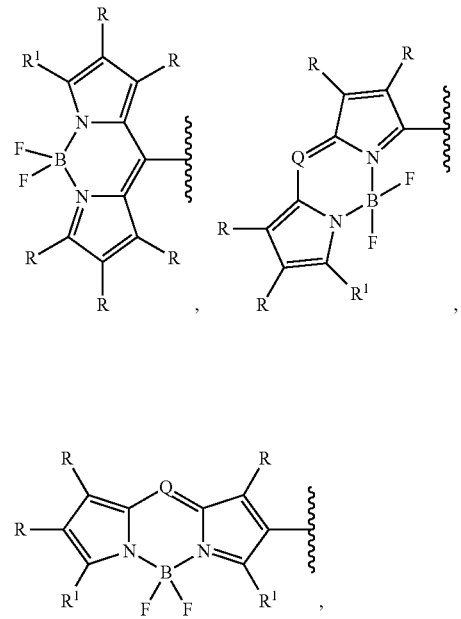

-continued

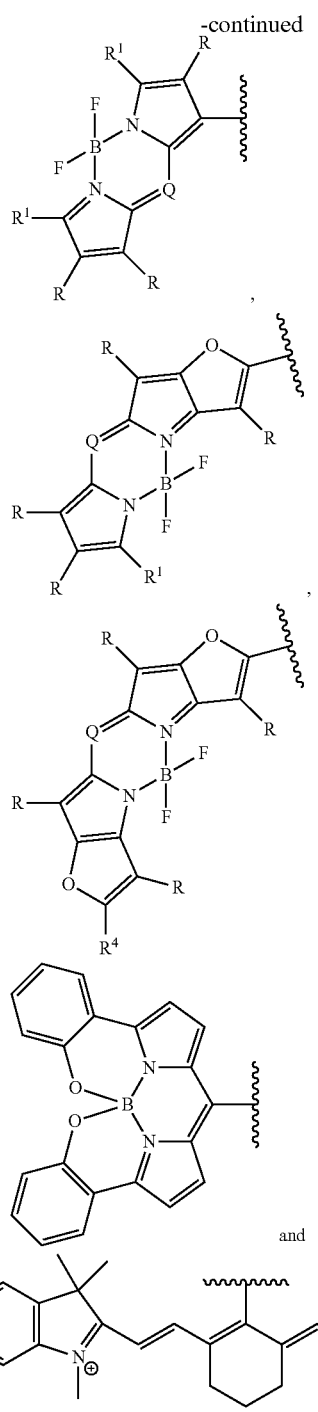

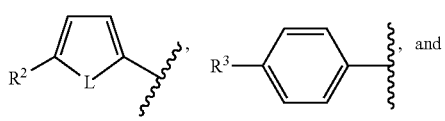

wherein R is selected from the group consisting of H, Me, Et, Br and I.
Q is selected from the group consisting of N, CH, C-Me, C-Et, C—CF$_3$, C-Ph
R$^1$ is selected from the group consisting of

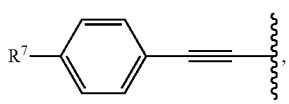, and

-continued

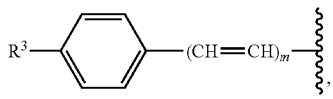

L is selected from the group consisting of O, S, NH and NMe;

R$^2$ is selected from the group consisting of H, Me, and Et;

R$^3$ is selected from the group consisting of H, OMe, OEt, and NMe$_2$;

R$^4$ is selected from the group consisting of H, Me, Et, Ph or p-methoxy-phenyl; and m is an integer from 1 to 5.

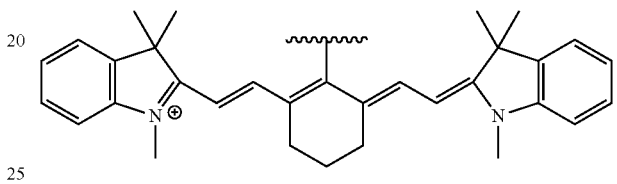

(or other positively charged fluorophores) may also include a negatively charged counterion, such as Cl$^-$.

FORMULA III

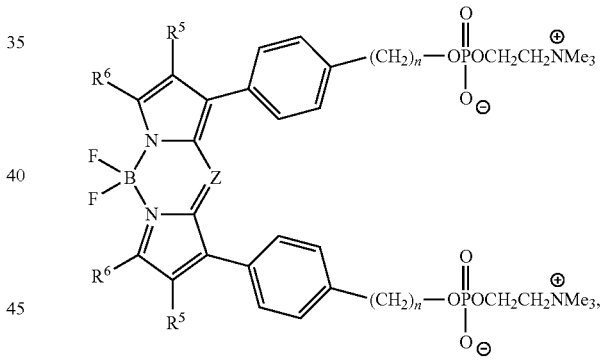

wherein R$^5$ is selected from the group consisting of H, Me, Et, Br and I;

R$^6$ is selected from the group consisting of H, Me, Et, p-methoxy-phenyl, p-(N,N-dimethylamino)-phenyl and wherein R$^7$ is selected from the group consisting of H, Me, OMe, and Me$_2$N.

FORMULA IV

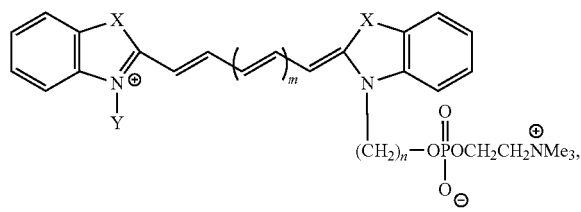

wherein n is an integer between 7 and 23;
m is an integer between 0 and 4;
X is selected from the group consisting of O, S, CMe$_2$, and C=CH$_2$;
Y is selected from the group consisting of Me, Et, Pr, i-Pr and

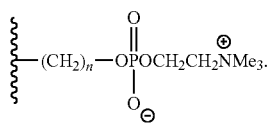

FORMULA V

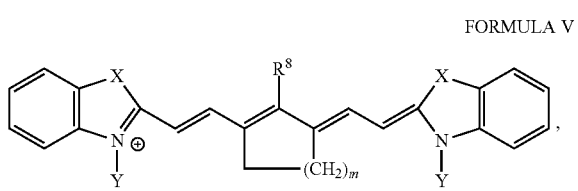

wherein m is an integer between 0 and 4;
X is selected from the group consisting of O, S, CMe$_2$ and C=CH$_2$;
Y is selected from the group consisting of Me, Et, Pr and i-Pr;
R$^8$ is selected from the group consisting of

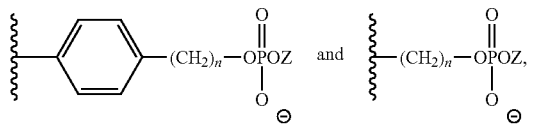

wherein n is an integer between 7 and 23; and
Z is selected from the group consisting of

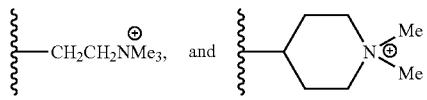

FORMULA VI

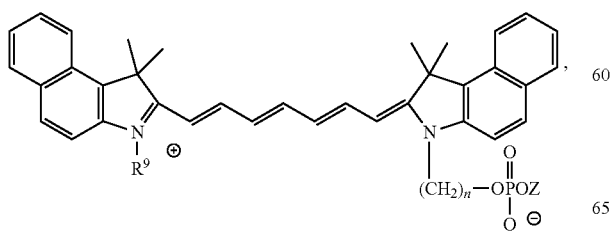

wherein n is an integer between 7 and 23
R$^9$ is selected from the group consisting of Me, Et and

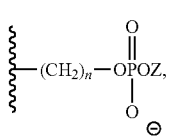

Z is selected from the group consisting of

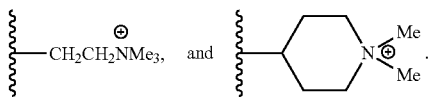

Presently preferred compounds include:

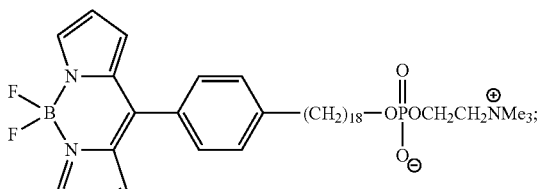

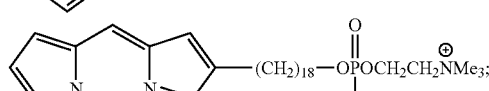

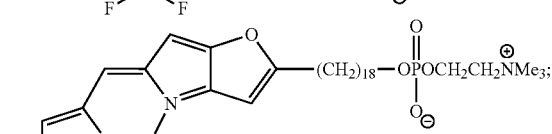

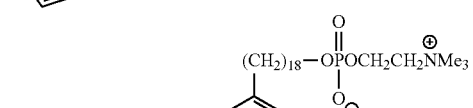

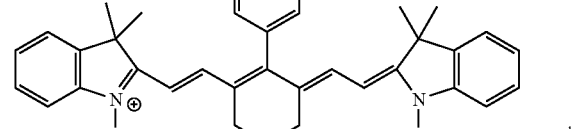

; and

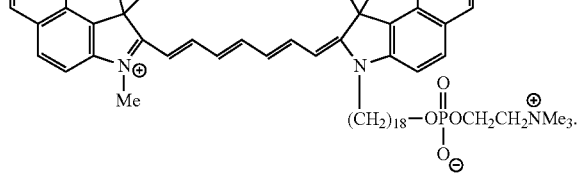

The particularly preferred compounds are

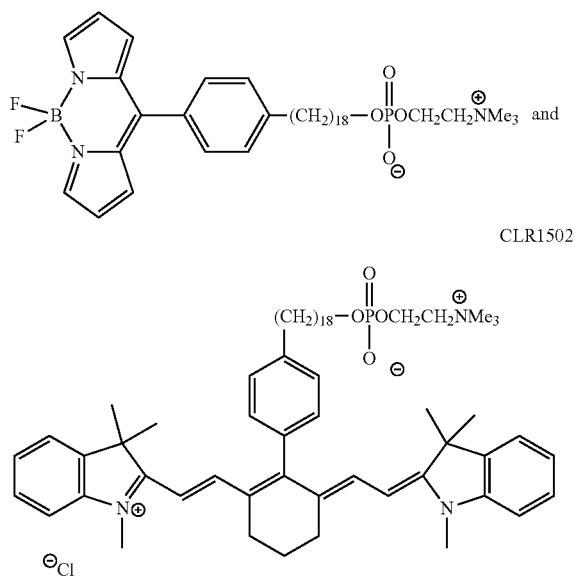

CLR1501

CLR1502

It is to be understood that the presence of counterions (e.g., Cl⊖) is optional, and the invention encompasses compounds with and without counterions.

The fluorescent compounds according to the present invention generally exhibit fluorescence at a wavelength of about 300 nm to about 1000 nm. In one embodiment, the first wavelength is about 400 nm to about 900 nm. Also, the second wavelength is about 400 nm to 1100 nm.

It is to be understood that the present invention encompasses the compounds in any racemic, optically-active, polymorphic, or stereroisomeric forms, or mixtures thereof. In one embodiment, the fluorescent phospholipid compounds may include pure (R)-isomers. In another embodiment, the fluorescent phospholipid compounds may include pure (S)-isomers. In another embodiment, the fluorescent phospholipid compounds may include a mixture of the (R) and the (S) isomers. In another embodiment, the fluorescent phospholipid compounds may include a racemic mixture comprising both (R) and (S) isomers. It is well known in the art how to prepare optically-active forms (for example, by resolution of the racemic form by recrystallization techniques, by synthesis from optically-active starting material, by chiral synthesis, or by chromatographic separation using a chiral stationary phase).

The compounds of the invention can exist in unsolvated as well as solvated forms, including hydrated forms, e.g., hemi-hydrate. In general, the solvated forms, with pharmaceutically acceptable solvents such as water, ethanol, and the like are equivalent to the unsolvated forms for the purposes of the invention.

Preferably, the compounds of the invention are ambiphilic.

Certain compounds of the invention also form pharmaceutically acceptable salts, e.g., acid addition salts. For example, the nitrogen atoms may form salts with acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous hydroxide potassium carbonate, ammonia, and sodium bicarbonate. The free base forms differ from their respective salt forms somewhat in certain physical properties, such as solubility in polar solvents, but the acid salts are equivalent to their respective free base forms for purposes of the invention. (See, for example S. M. Berge, et al., "Pharmaceutical Salts," *J. Pharm. Sci.*, 66:1-19 (1977).

Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulfuric acid, methanesulfonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts, alkaline earth metal salts, e.g. calcium or magnesium salts; and salts formed with suitable organic ligands, e.g. quaternary ammonium salts.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, S. M. Berge et al. describe pharmaceutically acceptable salts in detail in *J. Pharmaceutical Sciences*, 1977, 66: 1 et seq. The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylammonium, dimethylammonium, trimethylammonium, triethylammonium, diethylammonium, and ethylammonium among others. Other representative organic amines useful for the formation of base addition salts include ethylenediamine, ethanolamine, diethanolamine, piperidine, piperazine and the like.

Where the compounds according to the invention have at least one asymmetric center, they may accordingly exist as enantiomers. Where the compounds according to the invention possess two or more asymmetric centers, they may additionally exist as diastereoisomers. It is to be understood that all such isomers and mixtures thereof in any proportion are encompassed within the scope of the present invention.

The invention also includes N-oxides of the amino substituents of the compounds described herein. Pharmaceutically acceptable salts can also be prepared from the phenolic compounds by treatment with inorganic bases, for example, sodium hydroxide. Also, esters of the phenolic compounds can be made with aliphatic and aromatic carboxylic acids, for example, acetic acid and benzoic acid esters.

A "diagnostically effective amount" means an amount of a compound that, when administered to a subject for screening for tumors, is sufficient to provide a detectable distinction between a benign structure and a malignant tumor. The "diagnostically effective amount" will vary depending on the compound, the condition to be detected, the severity or the condition, the age and relative health of the subject, the route and form of administration, the judgment of the attending medical or veterinary practitioner, and other factors.

A compound of the present invention is administered to a subject in a diagnostically effective amount. A compound of the present invention can be administered alone or as part of a pharmaceutically acceptable composition. In addition, a compound or composition can be administered all at once, as for example, by a bolus injection, multiple times, such as by a series of tablets, or delivered substantially uniformly over a period of time, as for example, using transdermal delivery. It is also noted that the dose of the compound can be varied over time. A compound of the present invention can be administered using an immediate release formulation, a controlled release formulation, or combinations thereof. The term "controlled release" includes sustained release, delayed release, and combinations thereof. In preferred embodiments, a fluorescent phospholipid compound of the present invention is combined with a pharmaceutically acceptable carrier to produce a pharmaceutical preparation for parenteral administration.

The term "pharmaceutically acceptable" means that which is useful in preparing a pharmaceutical composition that is generally safe, non-toxic, and neither biologically nor otherwise undesirable and includes that which is acceptable for veterinary as well as human pharmaceutical use. The terms "pharmaceutically acceptable salts" or "prodrugs" includes the salts and prodrugs of compounds that are within the scope of sound medical judgment, suitable for use with subjects without undue toxicity, irritation, allergic response, and the like, commensurate with a reasonable benefit/risk ratio, and effective for their intended use as well as the zwitterionic forms, where possible, of the compounds.

As defined herein, "contacting" means that the fluorescent phospholipid compound used in the present invention is introduced to a sample containing cells or tissue in a test tube, flask, tissue culture, chip, array, plate, microplate, capillary, or the like, and incubated at a temperature and time sufficient to permit binding of the fluorescent phospholipid compound to a receptor or intercalation into a membrane. Methods for contacting the samples with the fluorescent phospholipid compound or other specific binding components are known to those skilled in the art and may be selected depending on the type of assay protocol to be run, Incubation methods are also standard and are known to those skilled in the art.

In another embodiment, the term "contacting" means that the fluorescent phospholipid compound used in the present invention is introduced into a patient receiving treatment, and the compound is allowed to come in contact in vivo. In further embodiment, the term "contacting" means that the fluorescent phospholipid compound used in the present invention is introduced into a patient requiring screening for tumors, and the compound is allowed to come in contact in vivo.

The invention also generally relates to compositions comprising the compounds of the present invention.

As used herein, the term "composition" is intended to encompass a product comprising the specified ingredients in the specified amounts, as well as any product which results, directly or indirectly, from a combination of the specified ingredients in the specified amounts.

Compositions of the present invention may be prepared as a single unit dose or as a plurality of single unit doses. As used herein, a "unit dose" means a discrete amount of the composition comprising a predetermined amount of the active ingredient. The amount of the active ingredient is generally equal to the dosage of the active ingredient that would be administered to a patient or a fraction thereof.

As used herein, "pharmaceutical composition" means therapeutically effective amounts of the tumor-specific phospholipid ether analog together with suitable diluents, preservatives, solubilizers, emulsifiers, and adjuvants, collectively "pharmaceutically-acceptable carriers." As used herein, the terms "effective amount" and "diagnostically effective amount" refer to the quantity of active agent sufficient to yield a desired effect without undue adverse side effects such as toxicity, irritation, or allergic response. The specific "effective amount" will vary with such factors as the particular condition being diagnosed, the physical condition of the subject, the species of the subject, the nature of concurrent therapy (if any), and the specific formulations employed and the structure of the compounds or its derivatives. The optimum effective amounts can be readily determined by one of ordinary skill in the art with routine experimentation.

Compositions of the present invention may be liquids or lyophilized or otherwise dried formulations and include diluents of various buffer content (e.g., Tris-HCl, acetate, phosphate), pH and ionic strength, additives such as albumin or gelatin to prevent absorption to surfaces, detergents (e.g., Tween 20™, Tween 80™, Pluronic F68™, bile acid salts), solubilizing agents (e.g., glycerol, polyethylene glycerol), anti-oxidants (e.g., ascorbic acid, sodium metabisulfite), preservatives (e.g., Thimerosal™, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

In a preferred embodiment, compositions of the present invention comprise a compound of the present invention, polysorbate, ethanol, and saline.

Also encompassed by the invention are methods of administering particulate compositions coated with polymers (e.g., poloxamers or poloxamines). Other embodiments of the compositions incorporate particulate forms protective coatings, protease inhibitors or permeation enhancers for various routes of administration, including topical, parenteral, pulmonary, nasal and oral. In some embodiments, the pharmaceutical composition is administered parenterally, paracancerally, transmucosally, tansdermally, intramuscularly, intravenously, intradermally, subcutaneously, intraperitonealy, intraventricularly, intracranially and intratumorally.

Further, as used herein "pharmaceutically acceptable carriers" are well known to those skilled in the art and include, but are not limited to, 0.01-0.1 M and preferably 0.05 M phosphate buffer or 0.9% saline. Additionally, such pharmaceutically acceptable carriers may be aqueous or non-aqueous solutions, suspensions, and emulsions, Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media.

Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants-, collating agents, inert gases and the like.

Controlled or sustained release compositions according to the invention include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors. Other embodiments of the compositions according to the invention incorporate particulate forms, protective coatings, protease inhibitors or permeation enhancers for various routes of administration, including parenteral, pulmonary, nasal and oral.

Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark at al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The pharmaceutical preparation can comprise the fluorescent phospholipid compound alone, or can further include a pharmaceutically acceptable carrier, and can be in solid or liquid form such as tablets, powders, capsules, pellets, solutions, suspensions, elixirs, emulsions, gels, creams, or suppositories, including rectal and urethral suppositories. Pharmaceutically acceptable carriers include gums, starches, sugars, cellulosic material, and mixtures thereof. The pharmaceutical preparation containing the fluorescent phospholipid compound can be administered to a patient by, for example, subcutaneous implantation of a pellet. In a further embodiment, a pellet provides for controlled release of tumor-specific phospholipid ether analog over a period of time. The preparation can also be administered by intravenous, intraarterial, or intramuscular injection of a liquid preparation oral administration of a liquid or solid preparation, or by topical application. Administration can also be accomplished by use of a rectal suppository or a urethral suppository.

The pharmaceutical preparations administrable by the invention can be prepared by known dissolving, mixing, granulating, or tablet-forming processes. For oral administration, the tumor-specific phospholipid ether analogs or their physiologically tolerated derivatives such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous-, intra-arterial, or intramuscular injection), the tumor-specific phospholipid ether analogs or theft physiologically tolerated derivatives such as salts, esters, N-oxides, and the like are converted into a solution, suspension, or expulsion, if desired with the substances customary and suitable for this purpose, for example, solubilizers or other auxiliaries, Examples are sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The preparation of pharmaceutical compositions which contain an active component is well understood in the art. Such compositions may be prepared as aerosols delivered to the nasopharynx or as injectables, either as liquid solutions or suspensions; however, solid forms suitable for solution in, or suspension in, liquid prior to injection can also be prepared. The preparation can also be emulsified. Active therapeutic ingredients are often mixed with excipients which are pharmaceutically acceptable and compatible with the active ingredient. Suitable excipients are, for example, water, saline, dextrose, glycerol, ethanol, or the like or any combination thereof.

In addition, the composition can contain minor amounts of auxiliary substances such as wetting or emulsifying agents, pH buffering agents which enhance the effectiveness of the active ingredient.

Methods of Use

The compounds of the present invention may be used in a variety of diagnostic and therapeutic methods.

In one embodiment, the compounds may administered to the patient via either the enteral or parenteral routes (i.e., orally or via IV) for the endoscopic determination of the presence of internal malignancy. Examples include, but are not limited to, endoscopic diagnosis of malignancy in the colon, rectum, small bowel, esophagus, stomach, duodenum, uterus, pancreas and common bile duct, bronchi, esophagus, mouth, sinus, lung, bladder, kidney, abdominal cavity or thoracic (chest) cavity.

In a preferred embodiment, the invention provides a method for endoscopically distinguishing a benign tissue from a malignant tissue in a selected region by using an endoscope having at least two wavelength in a patient comprising the steps of: (a) administering a fluorescently labeled compound to the patient; (b) using a first technique to produce a visualization of the anatomy of the selected region using the first wavelength of an endoscope; (c) using a second technique to produce a visualization of the distribution of fluorescence produced by the fluorescently labeled compound; and (d) comparing the visualization of the anatomy of the selected region by the first wavelength to the visualization of the distribution of fluorescence by the second wavelength produced by the fluorescently labeled compound thereby distinguishing a benign tissue from malignant tissue. In this embodiment, preferably, the selected region is the gastro-intestinal tract and the respiratory tract. Preferably, a fluorescent phospholipid compound is injected intravenously a few hours before performing endoscopic examinations; more preferably from about 1 hour to about 4 hours.

In another embodiment, the compounds may be used to aid in the selection of biopsy tissues in the above-listed internal malignancies.

In yet another embodiment, the compounds may be administered to the patient via either the enteral or parenteral routes or via topical application for the visual and/or microscopically aided determination of the presence of malignant lesions on the skin. Examples include, but are not limited to, differentiating between benign and malignant lesions on the skin.

In another embodiment, the compounds may be used to aid in the selection of biopsy tissues in the above-listed skin malignancies.

In one embodiment, the invention generally relates to a A method of selecting a biopsy tissue in a region suspected of having a malignancy comprising (a) administering to a patient a fluorescent phospholipid ether compound; (b) using a first technique to produce a visualization of the anatomy of said region suspected of having said malignancy using the first wavelength of an endoscope; (c) using a second technique to produce a visualization of the distribution of fluorescence produced by the fluorescent phospholipid ether compound; and (d) comparing the visualization of the anatomy of said region suspected of having said malignancy by the first wavelength to the visualization of the distribution of fluorescence by the second wavelength produced by the fluorescent phospholipid ether compound thereby distinguishing a benign tissue from malignant tissue and allowing to choose the biopsy tissue.

In yet another embodiment, the compounds may be used to aid in the determination of malignant tissue margins during operative resection or Mohs surgery of such lesion.

In another embodiment, the compounds may be administered to the patient via either the enteral or parenteral routes (i.e. orally or IV) for the visual and or microscopic-aided determination of the presence of malignant tissue at the borders of known malignancies during surgery. Examples include, but are not limited to, the intraoperative determination of the borders of a malignancy to aid the complete biopsy and/or surgical resection of said malignancy. These methods can be used for any malignancy in any tissue of the human body.

In yet another embodiment, the compounds may be used to determine the presence of residual malignant stem cells in a pathological specimen that has been excised from the body of the patient and/or to determine the presence of residual cancer stem cells in situ in a patient.

For example, in one embodiment, the invention provides a method of determining the presence of residual malignant stem cells in a patient undergoing cancer therapy comprising (a) administering to a patient undergoing said cancer therapy the fluorescent phospholipid compound according to any of claims 1 through 4; (b) visualizing the tissue that was determined to be malignant prior to said cancer therapy; and (c) assessing accumulation of the fluorescent phospholipid compound in said tissue, wherein an accumulation of said fluorescent phospholipid compound in said tissue indicates a possible presence of residual malignant stem cells.

In yet another embodiment, the invention provides a method of determining the presence of residual malignant stem cells in a patient undergoing cancer therapy comprising (a) excising a pathological specimen from a patient undergoing said cancer therapy; b) incubating said pathological specimen with the fluorescent phospholipid compound according to any of claims 1 through 4; and (c) visualizing the distribution of said fluorescent phospholipid compound in said pathological specimen; wherein an accumulation of said fluorescent phospholipid compound in said specimen indicates a possible presence of residual malignant stem cells.

In yet another embodiment, the provided compounds may be used for tumor therapy response monitoring. In a preferred embodiment, the invention provides a method of monitoring response to a tumor therapy comprising (a) administering to a patient prior to said tumor therapy the fluorescent phospholipid compound according to any of claims 1 through 4; (b) providing said tumor therapy; (c) providing the fluorescent phospholipid compound according to any of claims 1 through 4 after the tumor therapy; and (d) assessing difference in accumulation of the fluorescent phospholipid compound from step (a) and step (c), wherein a greater accumulation of the phospholipid compound in step (a) versus lesser accumulation in step (c) indicates a positive response to the treatment and/or an effective treatment methodology.

The invention will further be described with the following examples. These examples are described for illustrative purposes only and should not be deemed to narrow or limit the scope of the present invention.

EXAMPLES

Example 1

Synthesis of 18-[p-(4,4-difluoro-4-bora-3a,4a-diaza-s-indacene-8-yl)-phenyl]-octadecyl phosphocholine (CLR1501)

The synthesis of CLR1501 was performed using Liebeskind-Srogl cross-coupling reaction (Liebeskind L S, Srogl J. Org. Lett., 2002, 4, 979-981) of 18-[p-(dihydroxyboryl)-phenyl]-octadecyl phosphocholine 2 with 8-thiomethyl-BODIPY 1 according to the published procedure (Pena-Cabrera E. et al. Org. Lett., 2007, 9, 3985-3988, J. Org. Chem., 2009, 74, 2053-2058).

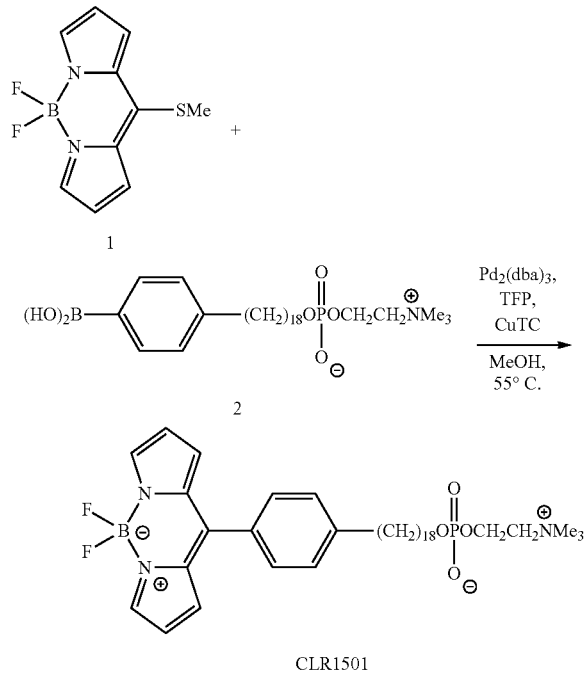

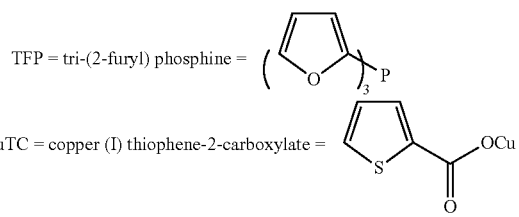

8-(Thiomethyl-4,4-difluoro-4-bora-3a,4a-diaza-s-indacene 1 was synthesized according to the literature procedure (Goud T. V., Tutar A., Biellman J. F. Tetrahedron, 2006, 62, 5084-5091).

A 20-ml round-bottom flask, equipped with a stir bar, was charged with 18-[p-(dihydroxyboryl)-phenyl]-octadecyl phosphocholine 2 (194 mg, 0.35 mmol), 8-(thiomethyl-4,4-difluoro-4-bora-3a,4a-diaza-s-indacene 1 (166 mg, 0.7 mmol), CuTC (133 mg, 0.7 mmol), Pd$_2$(dba)$_3$ (13 mg, 0.014 mmol) and TFP (16 mg, 0.07 mmol). The flask was evacuated under high vacuum for 15 min, refilled with dry nitrogen, and degassed methanol (5 ml) was added to the flask. The reaction mixture was stirred at 50° C. for 1.5 h, then cooled to the room temperature, diluted with 3-4 ml of chloroform and loaded on the silica gel column. The column was eluted with chloroform-methanol mixture (9:1, 8:2, 5:5) and finally with chloroform-methanol-water (65:25:4). Fractions containing product were combined, evaporated and the dark-red residue was dried under high vacuum. Yield of CLR1501: 169 mg (69%).

Example 2

Synthesis of CLR1502 Compound

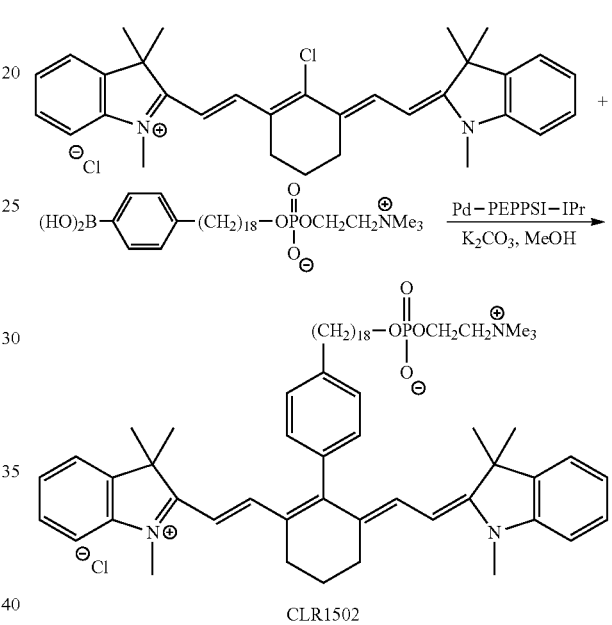

In air, 18[p-(dihydroxyboryl)-phenyl]-octadecyl phosphocholine (126 mg, 0.23 mmol), IR-775 chloride (177 mg, 0.34 mmol), powdered potassium carbonate (94 mg, 0.68 mmol) and Pd-PEPPSI-IPr (5 mg, 0.007 mmol) were weighed into a 10 mL round-bottom flask, and the flask was kept under high vacuum for 30 min. The flask was refilled with nitrogen and degassed methanol (7 ml) was added. The reaction mixture was stirred for 12 h at room temperature and checked by TLC for completion. The starting boronic acid was still present. More Pd-PEPPSI-IPr (1 mg) was added and stirring was continued for additional 10 h until completion. The reaction mixture was loaded onto silica gel column and eluted with CHCl$_3$-MeOH mixtures (9:1, 8:2, 5:5), 100 mL each and finally with CHCl$_3$-MeOH—H$_2$O (65:25:4), 188 mL and CHCl$_3$-MeOH—H$_2$O (100:65:15), 540 mL. Yield: 140 mg (44%).

CLR1502 can also be referred to as IR-775-CLR1501 conjugate. IR-775 is a commercial dye made by Sigma-Aldrich®.

While the other compounds have not yet been synthesized, it is envisioned that they can be easily synthesized with a reasonable expectation of success using known methods and the following teachings of the present invention:

Example 3

Prophetic Syntheses

Synthesis of BODIPY-Modified Alkyl Phospholipids

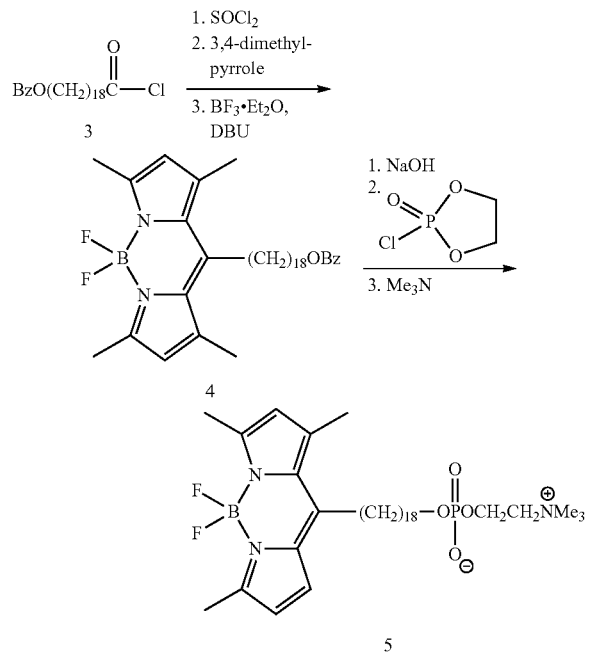

Synthesis of BODIPY-modified octadecyl phosphocholine without a phenyl ring between BODIPY fragment and alkyl chain is shown in Scheme 1. Synthesis can be performed according to the literature reference (C. Peters et al. *J. Org. Chem.*, 2007, 72, 1842-1845). The synthesis is started from a long-chain acid chloride 3 which is converted into the dipyrromethene by reaction with 2,5-dimethylpyrrole. This compound is used for the introduction of the $BF_2$ bridge, providing the BODIPY intermediate 4 which is converted into the phosphocholine 5.

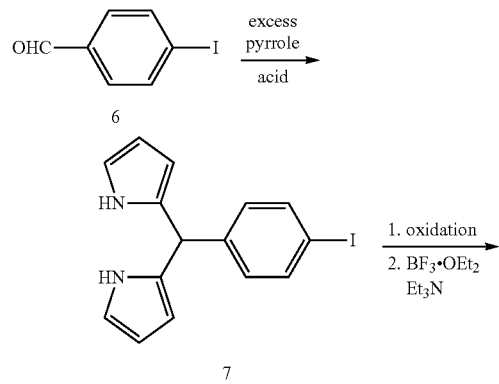

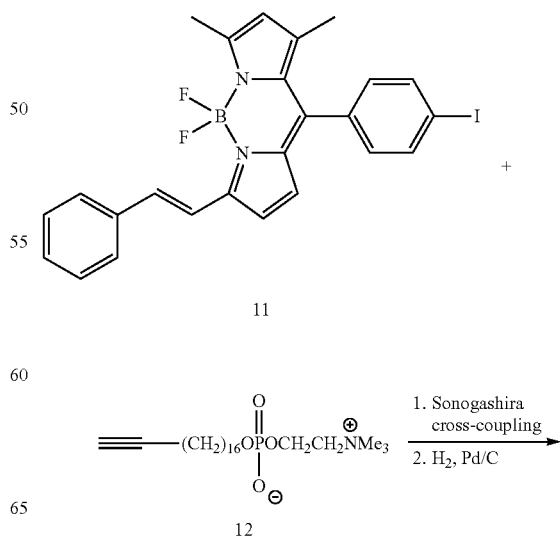

Synthesis of perifosine-like analog 10 is shown in Scheme 2. Condensation of 4-iodobenzaldehyde 6 with pyrrole in the presence of a catalytic amount of acid, followed by oxidation of 7 and chelation with $BF_3$ gives 8-(p-iodophenyl)-BODIPY intermediate 8 (Loudet A., Burgess K. *Chem. Rev.*, 2007, 107, 4891-4932). In the Sonogashira reaction, this intermediate is cross-coupled with acetylenic phospholipid 9 bearing a perifosine head group. Subsequent hydrogenation of the triple bond provides fluorescent phospholipid 10.

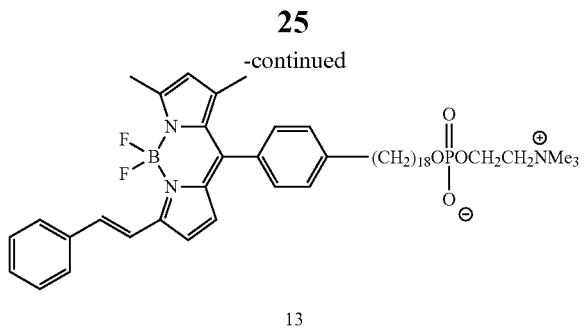

13

Synthesis of fluorescent alkyl phosphocholine with non-symmetrically substituted BODIPY 13 is shown in Scheme 3. The BODIPY core 11 can be synthesized according to the published procedure (Li Z., Bittman R. *J. Org. Chem.*, 2007, 72, 8376-8382). The rest of the synthesis is similar to the one shown in Scheme 2.

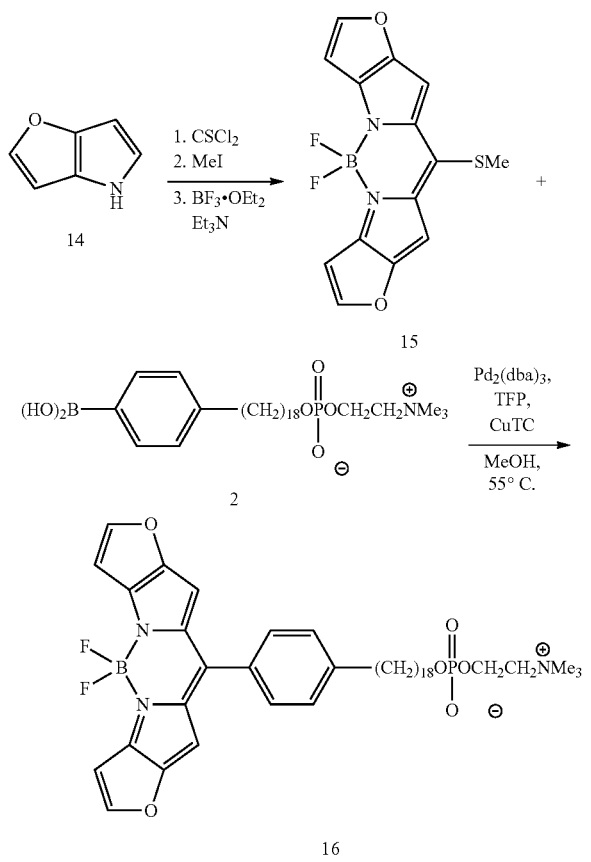

Scheme 4 provides an example of the synthesis of heteroaryl-fused BODIPY alkyl phospholipid 16. Hetreoaryl-fused BODIPY dyes have been described in the literature (Umezawa K, Matsui A, Nakamura Y, Citterio D, Suzuki K. *Chem. Eur. J.*, 2009, 15, 1096-1106; Umezawa K, Nakamura H, Makino H, Citterio D, Suzuki K. *J. Am. Chem. Soc.*, 2008, 130, 1550-1551), and they exhibit high extinction coefficients and high quantum yields in the far-red and near-IR regions of the spectrum. Synthesis of BODIPY intermediate 15 is based on the procedures provided in the literature (Umezawa K, Matsui A, Nakamura Y, Citterio D, Suzuki K. *Chem. Eur. J.*, 2009, 15, 1096-1106; Goud T. V., Tutar A., Biellman J. F. *Tetrahedron*, 2006, 62, 5084-5091). The synthesis of fluorescent alkyl phosphocholine 16 is performed using Liebeskind-Srogl cross-coupling reaction (Liebeskind L S, Srogl *J. Org. Lett.*, 2002, 4, 979-981) of 18-[p-(dihydroxyboryl)-phenyl]-octadecyl phosphocholine 2 with 8-thiomethyl-BODIPY 15 according to the published procedure (Pena-Cabrera E. et al. *Org. Lett.*, 2007, 9, 3985-3988, *J. Org. Chem.*, 2009, 74, 2053-2058).

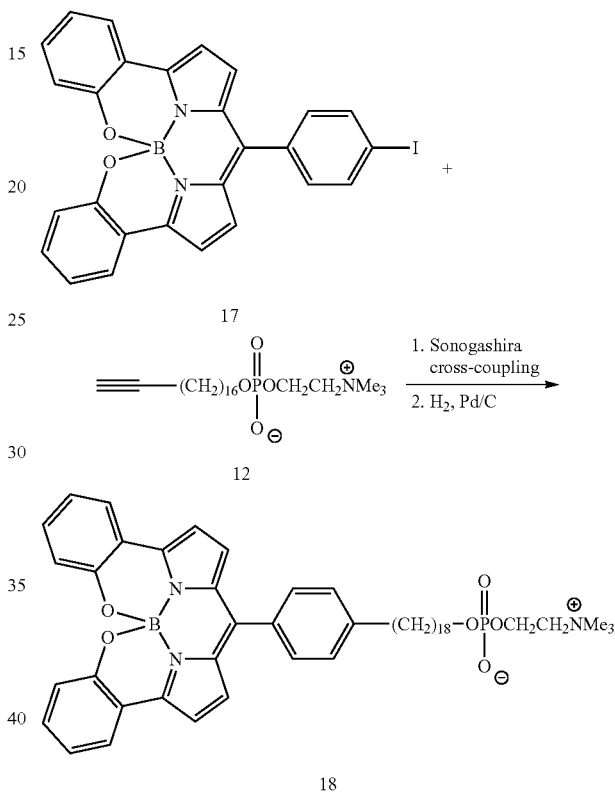

The synthesis of the fluorescent alkyl phospholipid bearing constrained BODIPY chromophore is shown in Scheme 5. The constrained BODIPY dye which is incorporated into 18 was shown to have a sharper, red-shifted, and more intense fluorescence emission than the parent $BF_2$ dye (Kim H, Burghart A, Welch M B, Reibenspies J, Burgess K. *Chem. Commun*, 1999, 1889-1890; Loudet A., Burgess K. *Chem. Rev.*, 2007, 107, 4891-4932). Synthessis of constrained BODIPY 17 is known in the literature ((Kim H, Burghart A, Welch M B, Reibenspies J, Burgess K. *Chem. Commun*, 1999, 1889-1890). The BODIPY compound 17 is cross-coupled with acetylenic alkyl phosphocholine 12 under conditions of Sonogashira reaction and the triple bond is hydrogenated to produce fluorescent phospholipid 18.

Synthesis of the Cyanine Dye-Modified Alkyl Phospholipids

This section describes prophetic synthesis of phospholipid ether analogs conjugated with cyanine dyes. Cyanines are popular sources of long-wavelength fluorophores with the excitation bands in the range of 600-900 nm (Goncalves M S. *Chem. Rev.*, 2009, 109, 190-212; Ballou B, Ernst L A, Waggoner A S. *Curr. Med. Chem.*, 2005, 12, 795-805; Frangioni J V. *Curr. Opin. Chem. Biol.*, 2003, 7, 626-634; Mishra A. et al. *Chem. Rev.*, 2000, 100, 1973-2011). Examples of phospholipid ether analogs conjugated to cyanine dyes include rigid (3) and non-rigid (XX) polymethyne structures.

Scheme 6

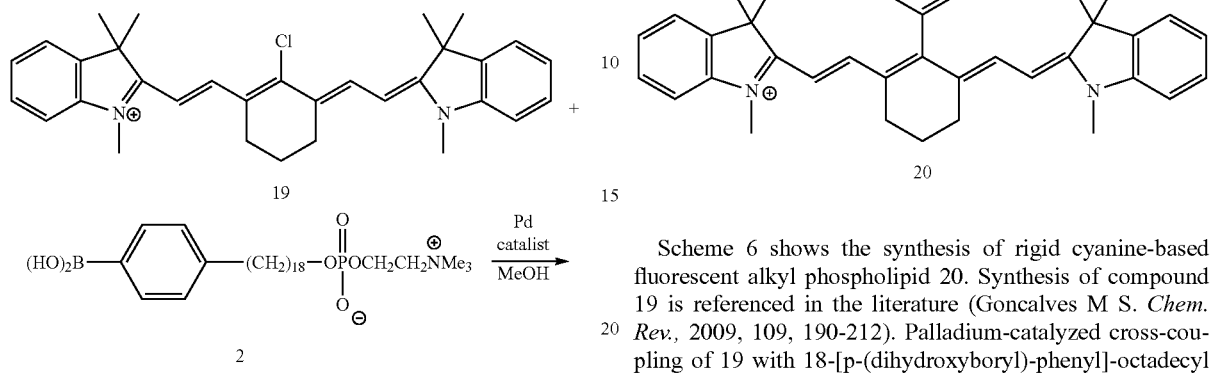

Scheme 6 shows the synthesis of rigid cyanine-based fluorescent alkyl phospholipid 20. Synthesis of compound 19 is referenced in the literature (Goncalves M S. *Chem. Rev.*, 2009, 109, 190-212). Palladium-catalyzed cross-coupling of 19 with 18-[p-(dihydroxyboryl)-phenyl]-octadecyl phosphocholine 2 provides fluorescent phospholipid 20.

Scheme 7

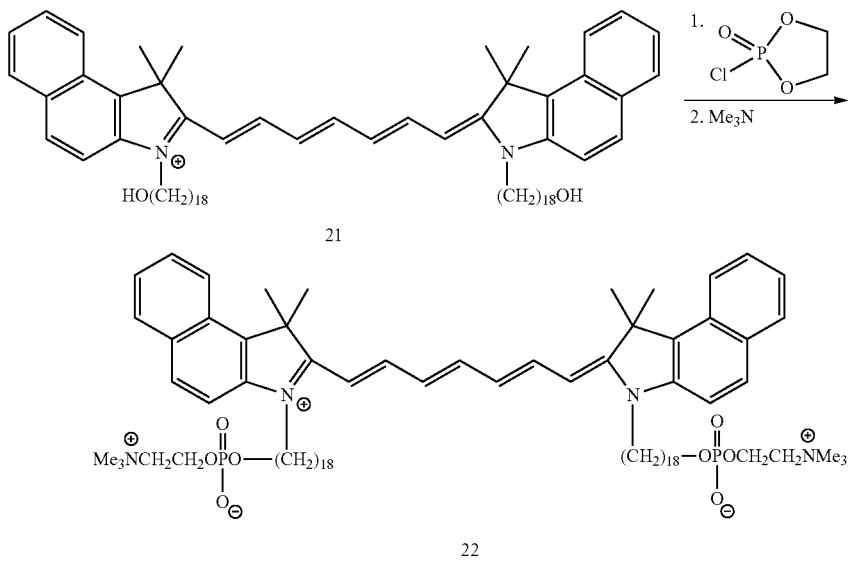

Synthesis of fluorescent phospholipid conjugated with non-rigid cyanine dye is shown in Scheme 7. Compound 21 bearing two long-chain alcohols is converted into the bis-phosphocholine analog 22. Compound 22 is a bis-alkyl phosphocholine derivative of Indocyanine Green (ICG, also known as IR-125) which is the only cyanine fluorochrome approved by the FDA.

Scheme 8

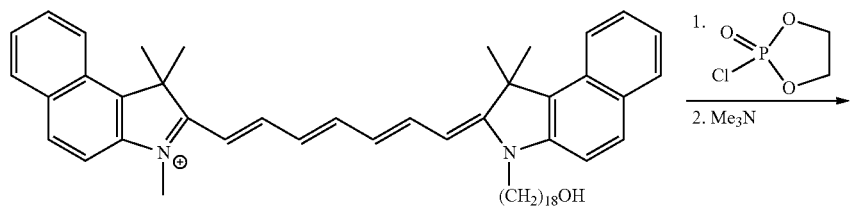

-continued

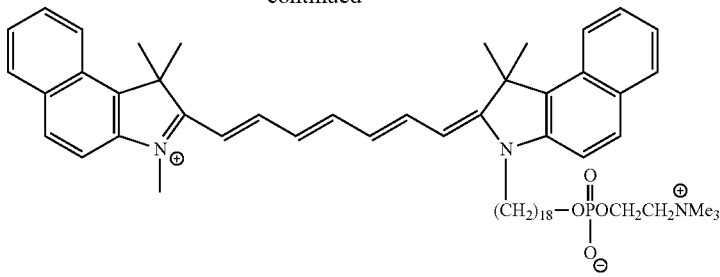

24

Another example shown in Scheme 8 includes mono-alkyl phosphocholine derivative of Indocyanine Green 24.

Example 4

In Vitro Studies with CLR1501

Experimental Conditions

To study the distribution of CLR1501 in cancer skin cells versus normal skin cells, CLR1501 was introduced into skin melanoma (A375) and normal skin (704sk) cells, purchased from ATCC. Both cells were maintained at 37° C. in DMEM media supplemented with 10% FBS and 5% $CO_2$. Before imaging, the cells were removed from flasks with 0.25% trypsin and were allowed to grow overnight on the slides (Ibidi, microslides VI flat, Catalog No: 80626). The next day, the media was gently replaced with Phosphate Buffered Saline (PBS) and the cells were incubated with 7.5 μM of CLR1501 on DMEM media for 24 hours. CRL1501 was formulated with 0.4% of Polysorbate 20, 2% of ethanol and saline. After washing thoroughly with PBS, the cells were imaged using Bio-Rad Radiance 2100 MP Rainbow with 1 second exposure time.

Results

Figure 1B:
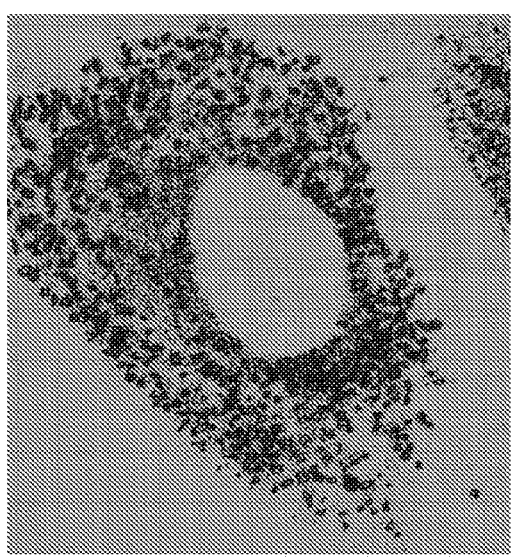
FIG. 1b depicts normal skin (704sk) cells after 24 hour incubation with CLR1501.

As FIGS. 1a and 1b demonstrate, in 704sk cells, the CLR 1501 appeared to be transported to the lysosomes where it was degraded (FIG. 1b). A375 cells showed internalization of CLR1501 into numerous fluorescent vesicles that are scattered throughout the cytoplasm (FIG. 1a).

Figure 2A:
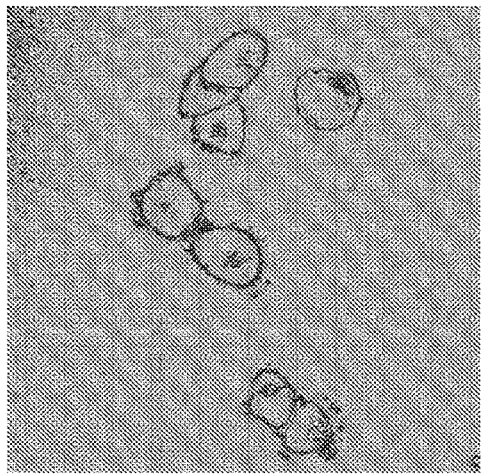
FIG. 2a depicts skin melanoma (A375) cells after 0.5 hour incubation with CLR1501.
Figure 2B:
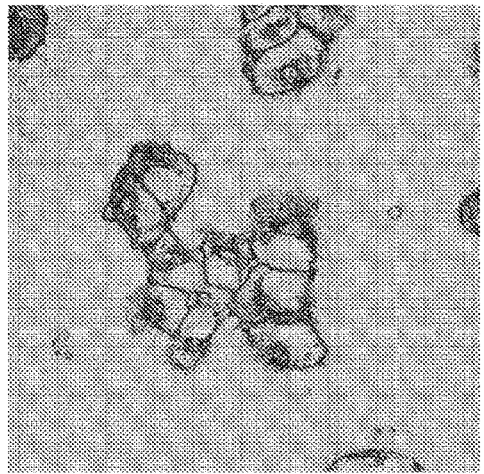
FIG. 2b depicts skin melanoma (A375) cells after 1 hour incubation with CLR1501.

FIGS. 2a and 2b demonstrate early time uptake profiles of CLR1501 in A375 cells half an hour (FIG. 2a) and one hour (FIG. 2b) after incubation. As FIG. 2a demonstrates, after half an hour, the signals are thin and limited at the plasma membrane. There are some endocytic vesicles formed near the plasma membrane. As FIG. 2b demonstrates, within one hour, the signals are not concentrated solely in the plasma membrane: intracellular structures are also observed. There is also a thicker signal associated with the plasma membrane.

Similar experiments were performed on several other cancerous cell lines: colorectal adenocarcinoma, uterine carcinoma, pancreatic carcinoma, ovarian adenocarcinoma, glioblastoma, clear cell carcinoma, and prostate adenocarcinoma. For comparison reasons, normal fibroblast cells were incubated with CLR1501.

Briefly, cells were plated overnight in micro slides VI (Ibidi, Verona, Wis.). The next day the cells were incubated with 5 μM of CLR1501 for 24 hours at 37° C. The cells were washed with PBS before the images were taken. The images were obtained using Nikon A1R confocal microscope. The length of exposure and intensity of the laser were similar among samples. CLR1501 was obtained using Alexa Fluor 488 filters (488 nm excitation-520 nm emission wavelength).

Table 1 illustrates intensity of signal emitted by CLR1501 in cancerous cell lines versus normal cells.

TABLE 1

| | Average grey intensity | Relative intensity to normal cells |
|---|---|---|
| NFA (normal cells) | 14.99 | 1 |
| Caki-2 | 151.56 | 10.11 |
| Ovcar-3 | 92.86 | 6.2 |
| Panc-1 | 143.65 | 9.58 |
| PC3 | 180.04 | 12.01 |

As Table 1 demonstrates, tumor cells took up CLR1501 6-12 times higher than normal fibroblast cells.

Figure 2C:
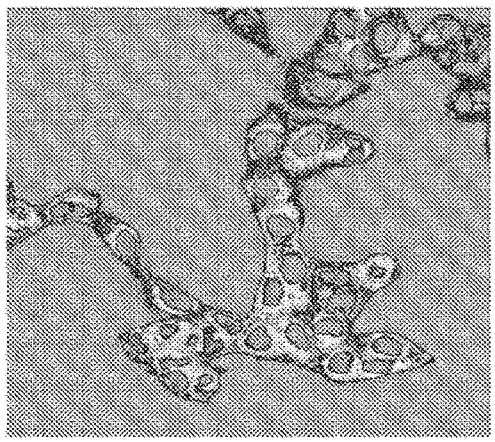
FIG. 2c depicts colorectal adenocarcinoma (HCT-116) cells after 24 hour incubation with CLR1501.
Figure 2D:
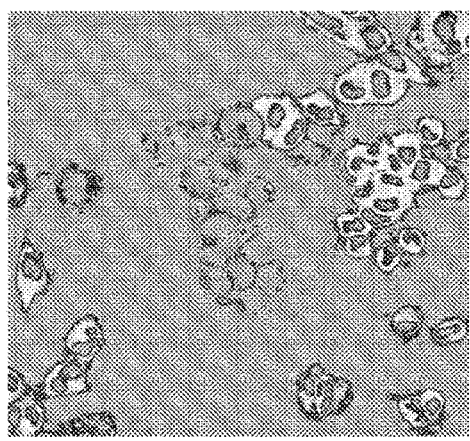
FIG. 2d depicts uterine carcinoma (MES SA/Dx5) cells after 24 hour incubation with CLR1501.
Figure 2E:
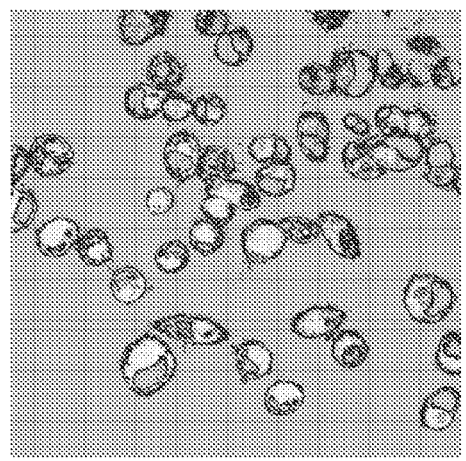
FIG. 2e depicts pancreatic carcinoma (Mia Paca-2) cells after 24 hour incubation with CLR1501.
Figure 2F:
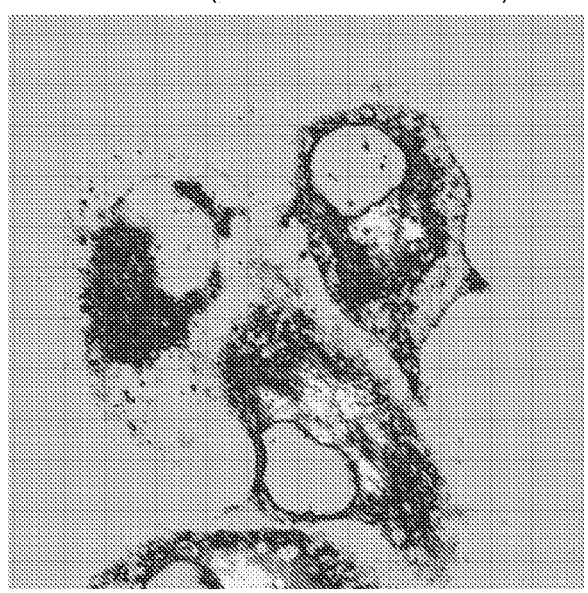
FIG. 2f depicts pancreatic carcinoma (Panc-1) cells after 24 hour incubation with CLR1501.
Figure 2G:
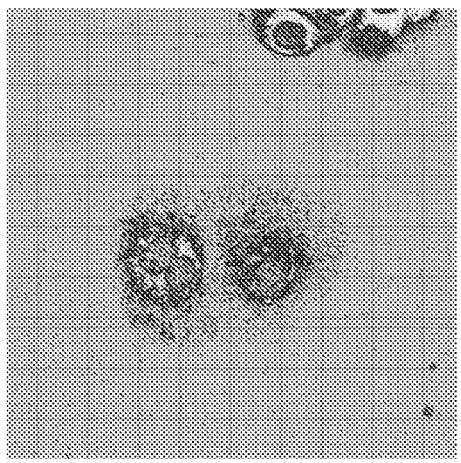
FIG. 2g depicts ovarian adenocarcinoma (Ovcar-3) cells after 24 hour incubation with CLR1501.
Figure 2H:
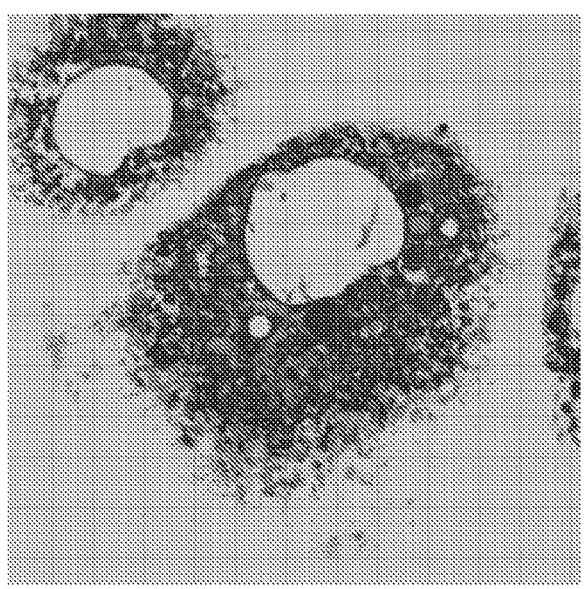
FIG. 2h depicts ovarian adenocarcinoma (Ovcar-3) cells after 24 hour incubation with CLR1501.
Figure 2I:
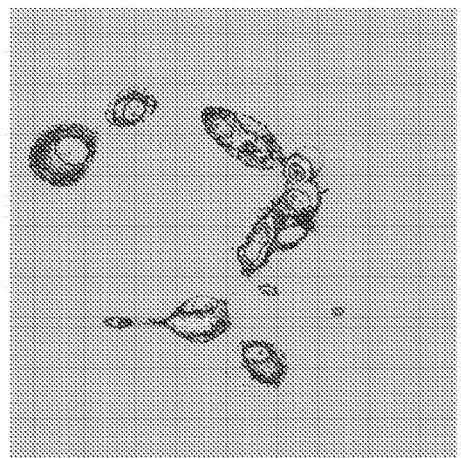
FIG. 2i depicts glioblastoma (U-87MG) cells after 24 hour incubation with CLR1501.
Figure 2J:
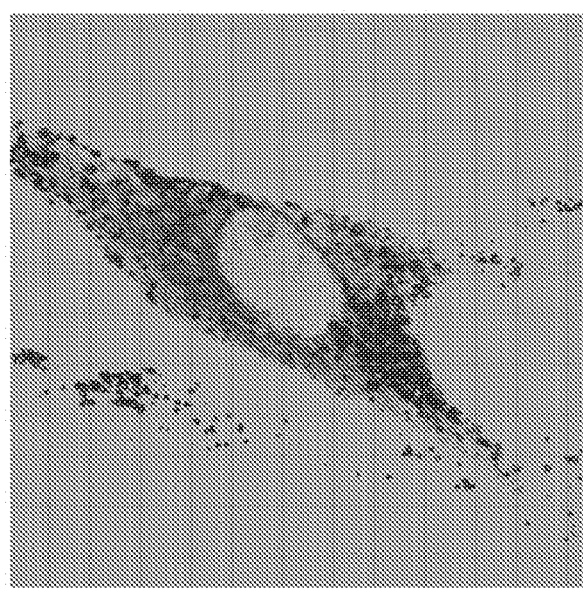
FIG. 2j depicts normal fibroblast (NFA) cells after 24 hour incubation with CLR1501.
Figure 2K:
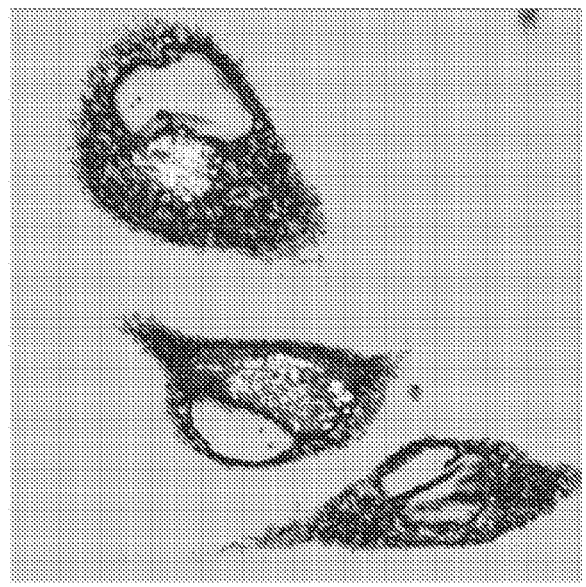
FIG. 2k depicts clear cell carcinoma (Caki 2) cells after 24 hour incubation with CLR1501.
Figure 2L:
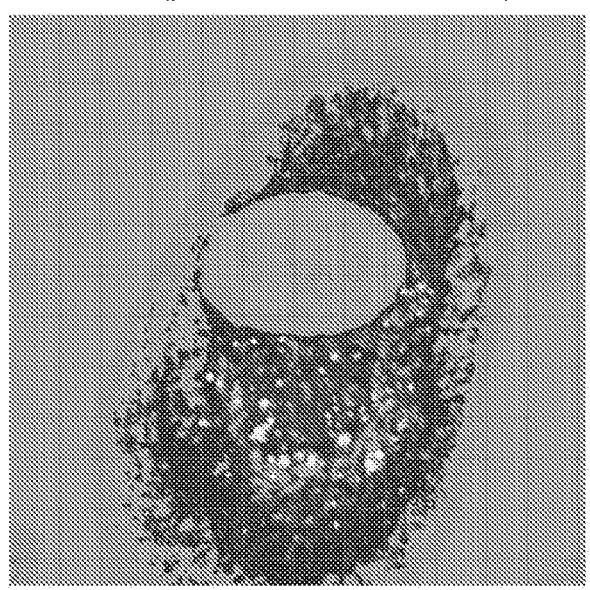
FIG. 2l depicts prostate adenocarcinoma (PC3) cells after 24 hour incubation with CLR1501.

FIG. 2c demonstrates the results for colorectal adenocarcinoma cell line (HCT-116);

FIG. 2d demonstrates the results for uterine sarcoma cell line (MES SA/DX-5);

FIG. 2e demonstrates the results for pancreatic carcinoma cell line (Mia Paca-2);

FIG. 2f demonstrates the results for pancreatic carcinoma cell line (Panc-1);

FIG. 2g demonstrates the results for ovarian adenocarcinoma cell line (Ovcar-3);

FIG. 2h demonstrates the results for ovarian adenocarcinoma cell line (Ovcar-3);

FIG. 2i demonstrates the results for glioblastoma cell line (U-87MG);

FIG. 2j demonstrates the results for normal fibroblast cell line (NFA);

FIG. 2k demonstrates the results for clear cell carcinoma cell line (Caki-2); and FIG. 2l demonstrates the results for prostate adenocarcinoma cell line (PC3).

FIGS. 2c-2i and 2k-2l demonstrate a significant uptake of CLR1501 in all of these cell lines. It is known that structurally related radioiodinated alkyl phosphocholine analog NM404 (18-p-(iodophenyl)-octadecyl phosphocholine) undergoes prolonged (>80 days in mouse models) and selective retention in a wide variety (37 out of 37) of xenograft and spontaneous primary and metastatic human and rodent tumor models. These experiments demonstrate that CLR1501, a fluorescent analog of NM404, displays a similar selective uptake and retention in tumor cell lines in vitro.

Figure 3:
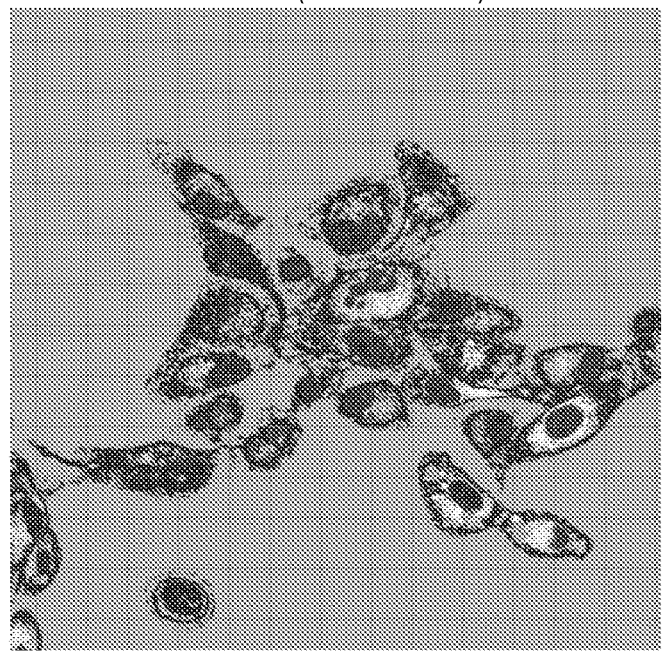
FIG. 3 depicts glioblastoma (U-87MG) cells after 48 hour incubation with CLR1501.

FIG. 3 demonstrates the results of an incubation of glioblastoma cells (U87MG) with CLR1501 for 48 hours in Eagle MEM media at 37° C. with 10% FBS and 5% $CO_2$. The following co-stained dyes were used: Hoechst 33342 (1 μg/mL) (nucleus; blue color), Mitotracker (25 nM) (mitochondria, red color) and Blue-White DPX (100 nM) (Endoplasmic Reticulum (ER), blue color) were diluted in PBS and added to the cells for 15 minutes. The cells were washed with PBS and imaged with Bio-Rad Radiance 2100 MP Rainbow.

The experiment demonstrated that that CLR1501 mostly accumulated in cytoplasm of the cells. The nucleus appeared blue while the red signals showed the distribution of mitochondria (colors are not reproduced on the photographs submitted with the PCT application). CLR1501 was co-localized with mitochondria and ER. The cyan signals (dark oval-shaped spots in FIG. 3) mostly distributed outside the nucleus near the nuclear membrane.

Figure 4:
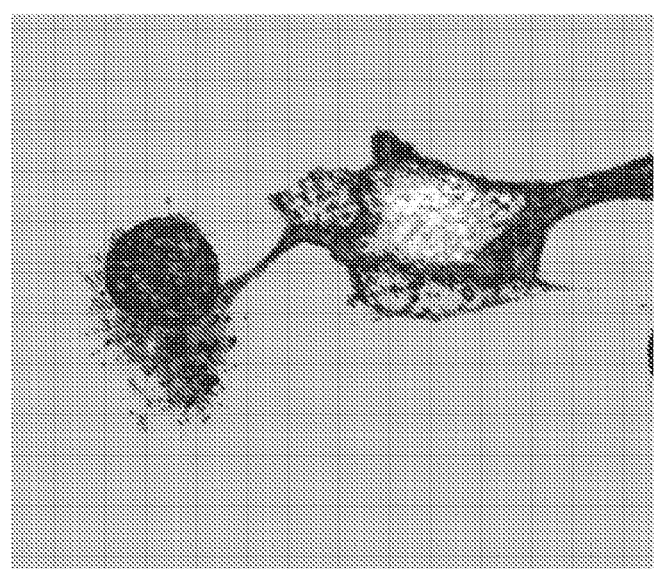
FIG. 4 depicts co-localization of CLR1501 with Normal Fibroblast (NFA) and prostate adenocarcinoma (PC3) cells.

FIG. 4 demonstrates the results of co-culturing NFA cells and PC3 cells, incubating them with CLR1501 and co-staining them with nucleus stain and mitochondria marker. Briefly, NFA and PC3 cell lines were co-cultured overnight on micro slide VI (Ibidi, Verona, Wis.). The next day, the cells were incubated with 5 μM of CLR1501 for 24 hours at 37° C. in complete media. The next day after washing with PBS, the cells were co-stained with nucleus stain (Hoechst 33342) and mitochondria marker (Mitotracker), (Invitrogen, Carlsbad, Calif.). The cells were observed using Nikon A1R confocal microscope. CLR1501 was excited and detected using Alexa-Fluor 488 filter, while nucleus stain and mitochondria stain were excited and detected using DAPI filter and Texas-Red filter, respectively. CLR1501 was not co-localized with nucleus in both normal and tumor cell lines. However, CLR1501 was co-localized with mitochondria in PC3 cell line but not with NFA.

Figure 5:
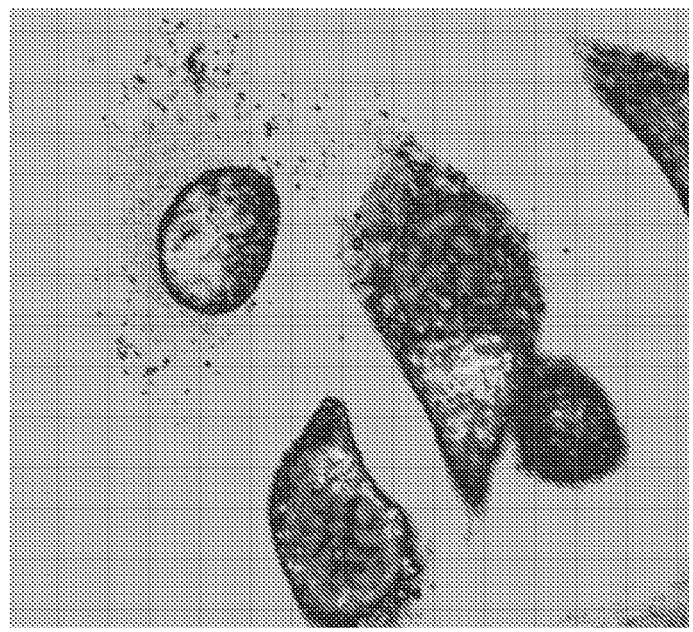
FIG. 5 depicts co-localization of CLR1501 with Normal Fibroblast (NFA) and clear cell carcinoma (Caki 2) cells.

FIG. 5 demonstrates the results of co-culturing NFA cells and Caki-2 cells, incubating them with CLR1501 and co-staining them with nucleus stain and lysosome marker. Briefly, NFA and Caki-2 cell lines were co-cultured overnight on micro slide VI (Ibidi, Verona, Wis.). The next day, the cells were incubated with 5 μM of CLR1501 for 24 hours at 37° C. in complete media. The next day after washing with PBS, the cells were co-stained with nucleus stain (Hoechst 33342) and lysosome marker (Lyso-tracker), (Invitrogen, Carlsbad, Calif.). The cells were observed using Nikon A1R confocal microscope. CLR1501 was excited and detected using Alexa-Fluor 488 filter while nucleus stain and lysosome stain were excited and detected using DAPI and Texas-Red filter, respectively. CLR 1501 was not co-localized with nucleus in both normal and tumor cell lines. However, CLR1501 was co-localized with lysosome in Caki-2 cell line but minimally with NFA.

The in vitro experiments have also demonstrated that CLR1501 does not penetrate inside of the nucleus.

Example 5

In Vivo Studies with CLR1501 and CLR1502

The inventors conducted in vivo studies of CLR1501 and CLR1502 distribution in athymic nude mice.

Athymic nude mice (Hsd: Athymic Nude-Fox1$^{nu}$), inoculated with Panc-1 (Pancreatic carcinoma), were injected with 150 μL of 6 mg/mL CLR1501 formulated in 0.4% Polysorbate 20, 2% ethanol and saline 24 hour and 96 hours prior to imaging. The fluorescence images were obtained using a Kodak In-Vivo Multispectral System FX. The system provides multispectral tuning of excitation light which is able to separate signals from the dye and from the body autofluorescence. Mice were anesthetized by inhalation of isofluorane. The dyes were excited at 570 nm.

Figure 6:
FIG. 6 depicts an image of an athymic nude mice inoculated with pancreatic carcinoma and injected with a composition comprising CLR1501.

FIG. 6 depicts the results of this experiment. Green signals show distribution of CLR1501 in tumors (marked with white arrows). The left image shows the mouse was injected 24 hours prior to imaging and the right image shows the mouse that was injected 96 hours prior to imaging. Black arrows show de-skinned area where CLR1501 accumulation can be seen in contrast.

The signal was found mostly in the tumors. However, signals were also found in some non-cancerous tissues, especially, skin. However, in the mouse injected 96 hours prior to imaging, the accumulation of CLR1501 in the tumor is more pronounced while the retention of the dye in other tissues is tremendously reduced.

Figure 7:
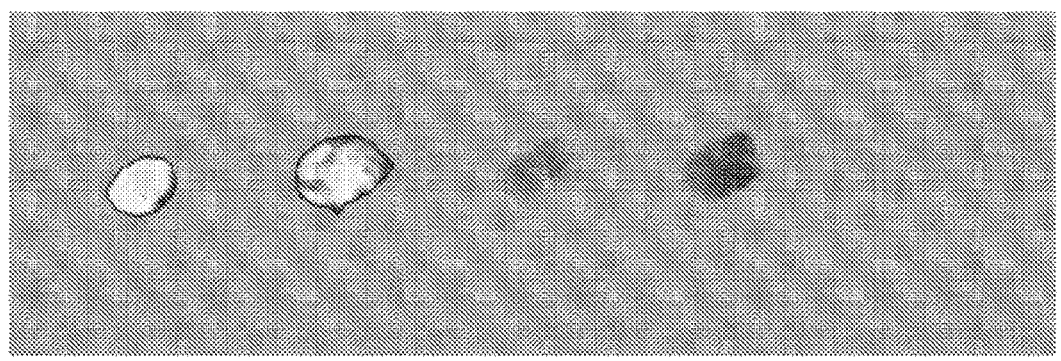
FIG. 7 depicts images of excised tumors of mice injected with CLR1501.

Some mice were orally administered 150 μL of CLR1501 at 6 mg/mL, mixed with 100 μL of oil in water phase emulsion (canola oil/saline) 24 and 96 hours, prior to imaging. FIG. 7 demonstrates the images of the excised tumors:

A: Tumor from mouse received IV injection CLR1501 24 hours prior imaging;

B: Tumor from mouse received IV injection of CLR 1501 96 hours prior imaging;

C: Tumor from mouse received CLR 1501 orally 24 hours prior imaging; and

D: Tumor from mouse received CLR 1501 orally 96 hours prior imaging.

Figure 8:
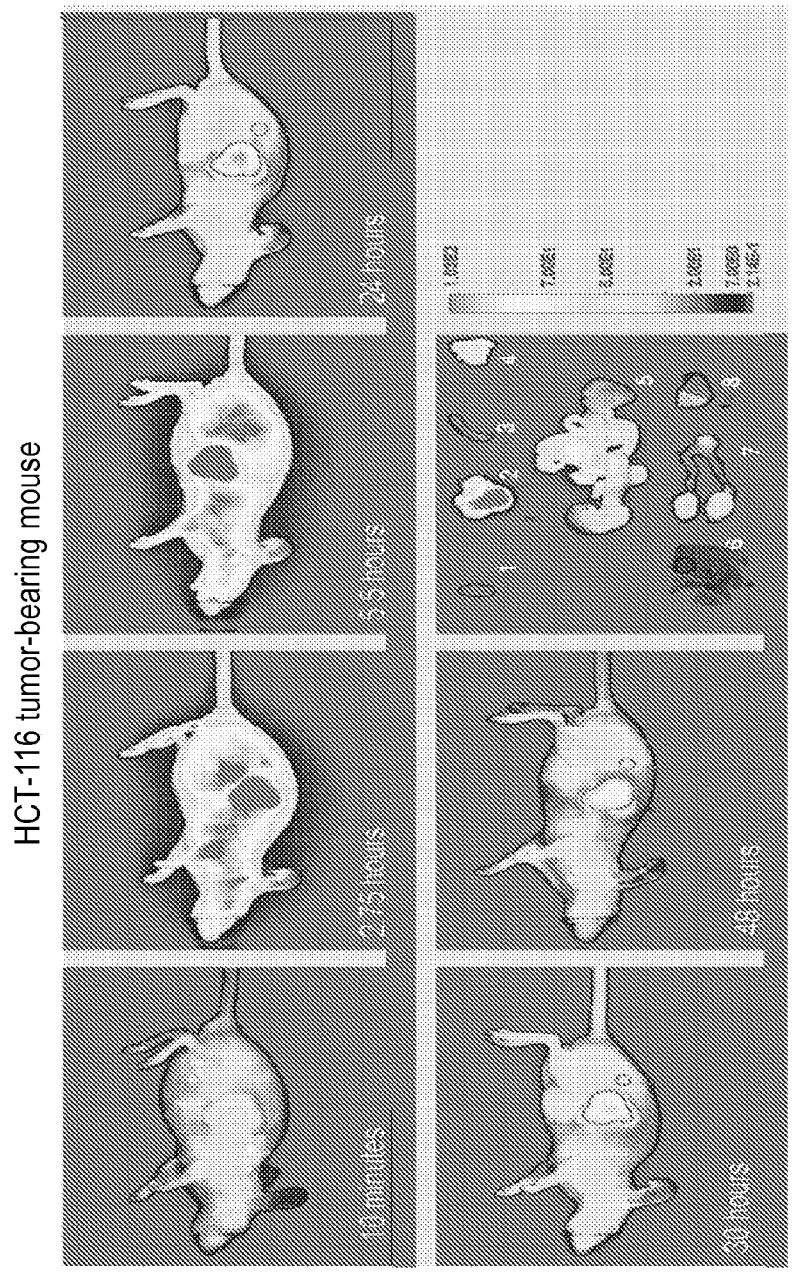
FIG. 8 depicts tumor co-localization of CLR1502 in human colorectal carcinoma (HCT-116) tumor bearing mouse.

FIG. 8 depicts tumor co-localization of CLR1502 in HCT-116 tumor-bearing mouse. Athymic nude mouse (Crl, NU-Foxn1$^{nu}$) was purchased from Charles River (Charles River, Portage, Mich.). The mouse was inoculated with $2 \times 10^6$ HCT-116 cells (human colorectal carcinoma). After 8 weeks, the mouse was injected with 1 mg of CLR1502 in 0.15 m solution. CLR1502 was excited at 780 and emitted at 800 nm. The intensity was monitored up to 48 hours using Pearl in vivo imaging system (Li-Cor Bioscience, Lincoln, Nebr.). At the end of 48 hours, organs from mouse were collected and imaged.

Over time, CLR1502 accumulated in tumor site, while it cleared out from the rest of normal organs, showing that CLR1502 is a tumor-specific imaging agent. The following organs were collected: heart, tumor, spleen, lung; GI tract (not flushed); skin, kidneys and liver.

Figure 9:
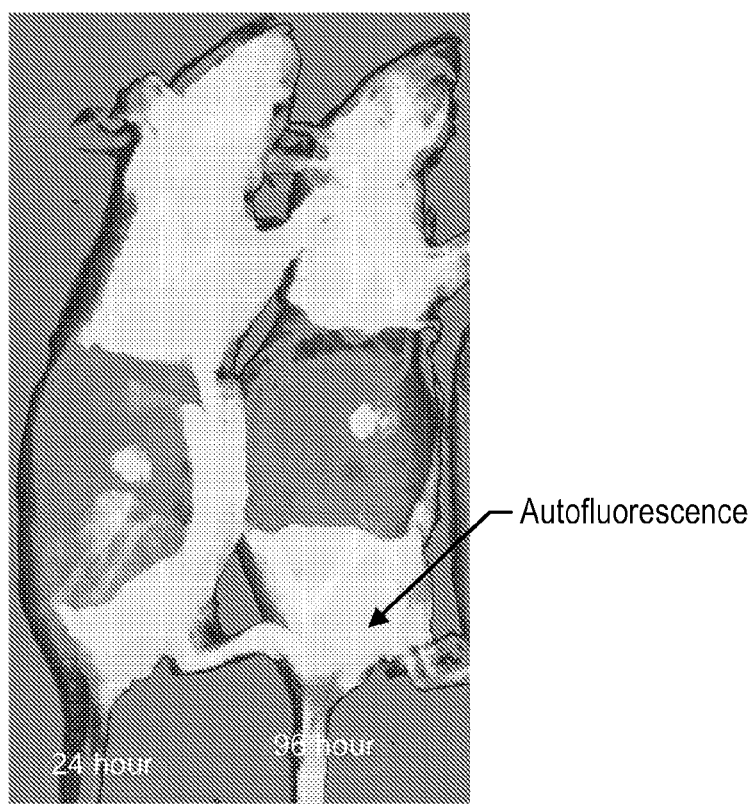
FIG. 9 depicts tumor co-localization of CLR1501 in de-skinned pancreatic carcinoma (Panc-1) tumor bearing mouse.

FIG. 9 depicts tumor co-localization of CLR1502 in de-skinned Panc-1 tumor-bearing mouse. Athymic nude mouse (Crl, NU-Foxn1$^{nu}$) was purchased from Charles River (Charles River, Portage, Mich.). The mouse was inoculated with $1 \times 10^6$ Panc-1 cells (human pancreatic carcinoma). After 8 weeks, the mouse was injected with 1 mg of CLR1501 in 0.15 mL solution. CLR1501 was excited at 480 and emitted at 520 nm. The intensity was monitored at 24 and 96 hours using Kodak in vivo imaging system (Carestream Health, Woodbridge, Conn.).

Over time, CLR1501 accumulated in tumor site, while it cleared out from the rest of normal organs. Skins surround tumors were removed to provide contrast signal from CLR1501. In this animal model, skin produces autofluorescence signal which overlaps with excitation and emission wavelengths of CLR1501.

Figure 10:
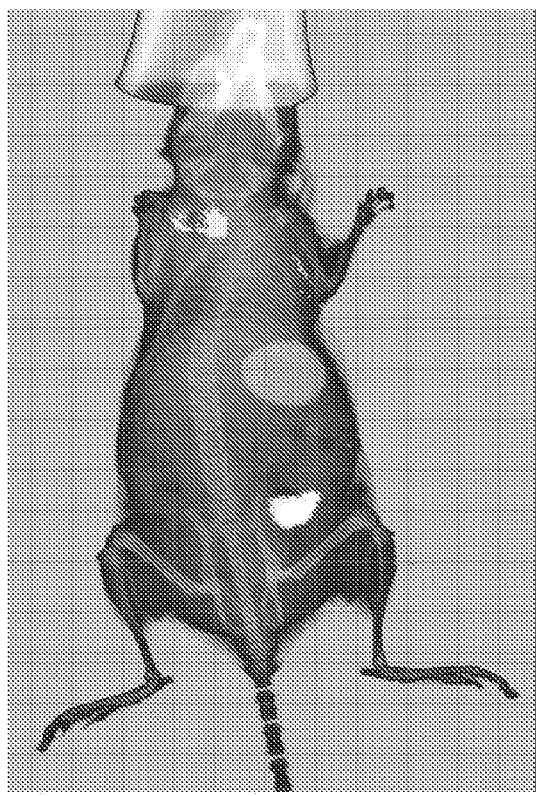
FIG. 10 depicts tumor co-localization of CLR1501 in de-skinned pancreatic carcinoma (Panc-1) tumor bearing mouse as shown using Kodak X-Sight 761

FIG. 10 depicts tumor co-localization of CLR1501 in athymic nude mouse. Athymic nude mouse (Crl, NU-Foxn1$^{nu}$) was purchased from Charles River (Charles River, Portage, Mich.). The mouse was inoculated with $1 \times 10^6$ Panc-1 cells (human pancreatic carcinoma) which were incubated with CLR1501 or Kodak X-Sight 761 or both CLR1501 and Kodak X-Sight 761 for 4 hours. The cells were harvested and inoculated in different spots. The signals from each dye were obtained using Kodak in vivo imaging system (Carestream Health, Woodbridge, Conn.). CLR1501 was excited at 480 and emitted at 520 nm while the Kodak X-Sight was excited at 750 and emitted at 830 nm.

This experiment showed that CLR1501 is taken up and retained in in vitro in cancer cells and continues to be retained in these cells after in vivo subcutaneous injection.

We claim:

1. A method of determining cancer in a subject, comprising:

administering to a subject a composition comprising a phospholipid ether compound selected from the group consisting of:

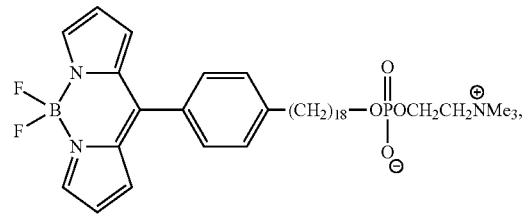

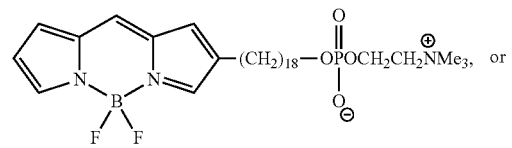

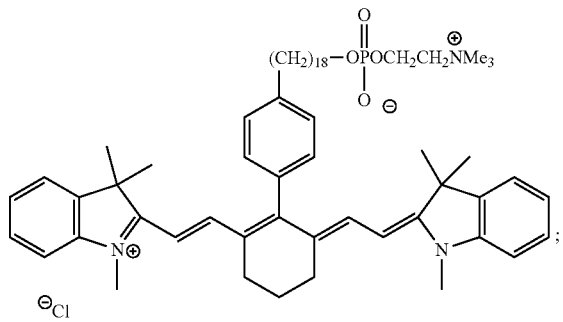

and determining cancer in the subject by detecting the phospholipid ether compound in the subject.

2. The method of claim 1, wherein the phospholipid ether compound has a structure:

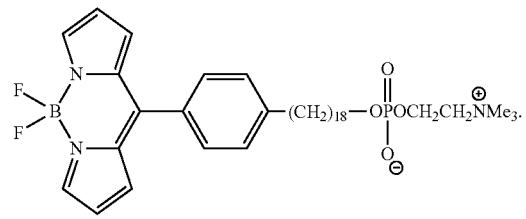

3. The method of claim 1, wherein the phospholipid ether compound has a structure:

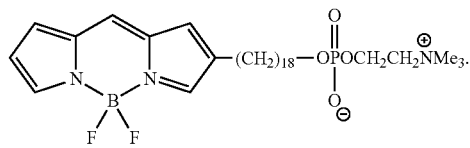

4. The method of claim 1, wherein the phospholipid ether compound has a structure:

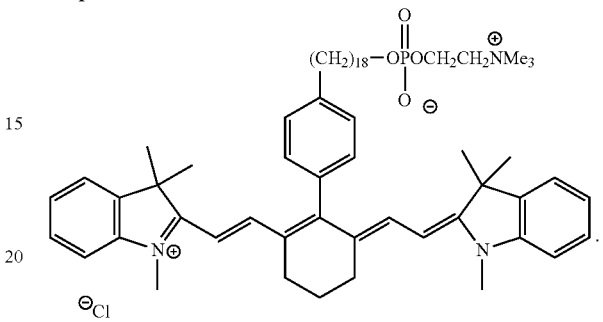

5. The method of claim 1, wherein the composition comprises a pharmaceutically acceptable carrier.

6. The method of claim 1, wherein the subject is human.

7. The method of claim 1, wherein the cancer is selected from the group consisting of melanoma, colorectal adenocarcinoma, uterine carcinoma, pancreatic carcinoma, ovarian adenocarcinoma, glioblastoma, clear cell carcinoma, and prostate adenocarcinoma.

8. The method of claim 1, wherein the phospholipid ether compound is detected using fluorescence.

9. A method of detection of a phospholipid ether compound within a subject, comprising:

administering to a subject a composition comprising a phospholipid ether compound selected from the group consisting of:

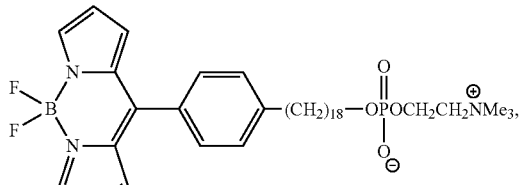

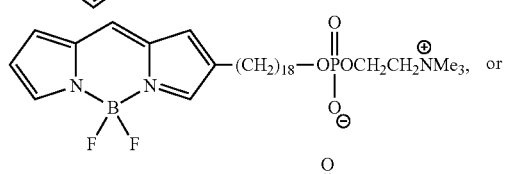

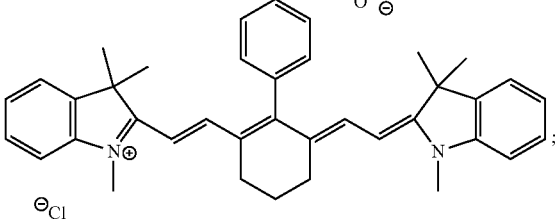

and
detecting retention of the phospholipid ether compound within an organ within the subject.

10. The method of claim 9, wherein the phospholipid ether compound has a structure

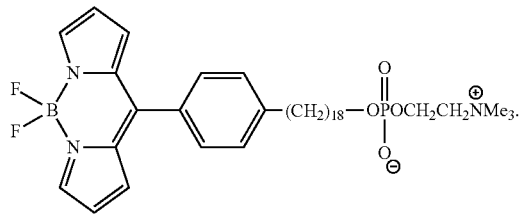

11. The method of claim 9, wherein the phospholipid ether compound has a structure:

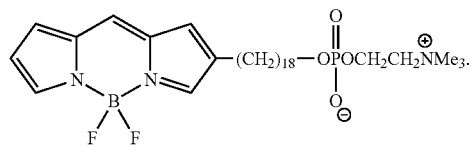

12. The method of claim 9, wherein the phospholipid ether compound has a structure:

13. The method of claim 9, wherein the composition comprises a pharmaceutically acceptable carrier.

14. The method of claim 9, wherein the subject is human.

15. The method of claim 9, wherein retention of the phospholipid ether compound is detected using fluorescence.

16. The method of claim 9, wherein the organ is selected from the group consisting of colon, rectum, small bowel, esophagus, stomach, duodenum, uterus, pancreas and common bile duct, bronchi, sinus, lung, bladder, kidney, abdominal cavity, and thoracic cavity.

* * * * *